United States Patent
Hourtash et al.

(10) Patent No.: US 9,931,172 B2
(45) Date of Patent: *Apr. 3, 2018

(54) SYSTEMS AND METHODS FOR USING THE NULL SPACE TO EMPHASIZE MANIPULATOR JOINT MOTION ANISOTROPICALLY

(71) Applicant: Intuitive Surgical Operations, Inc., Sunnyvale, CA (US)

(72) Inventors: Arjang M. Hourtash, Santa Clara, CA (US); Nitish Swarup, Sunnyvale, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/295,673

(22) Filed: Oct. 17, 2016

(65) Prior Publication Data

US 2017/0095303 A1    Apr. 6, 2017

Related U.S. Application Data

(63) Continuation of application No. 14/218,842, filed on Mar. 18, 2014, now Pat. No. 9,468,501.

(Continued)

(51) Int. Cl.
*B25J 15/02* (2006.01)
*G05B 19/04* (2006.01)
(Continued)

(52) U.S. Cl.
CPC .......... *A61B 34/37* (2016.02); *A61B 1/00193* (2013.01); *A61B 18/14* (2013.01);
(Continued)

(58) Field of Classification Search
CPC ......... A61B 34/30; A61B 34/70; A61B 34/76; A61B 34/20; A61B 2034/301;
(Continued)

(56) References Cited

U.S. PATENT DOCUMENTS

| 5,430,643 A | 7/1995 | Seraji |
| 5,784,542 A | 7/1998 | Ohm et al. |

(Continued)

FOREIGN PATENT DOCUMENTS

| CN | 101947787 A | 1/2011 |
| EP | 2332484 A2 | 6/2011 |

(Continued)

OTHER PUBLICATIONS

International Search Report and Written Opinion for Application No. PCT/US2014/31105, dated Jul. 1, 2014, 16 pages.

(Continued)

*Primary Examiner* — Marlon Fletcher
(74) *Attorney, Agent, or Firm* — Schwegman Lundberg & Woessner, P.A.

(57) ABSTRACT

Devices, systems, and methods for providing commanded movement of an end effector of a manipulator while providing a desired movement of one or more joints of the manipulator. Methods include calculating weighted joint velocities using a weighting matrix within the joint space to anisotropically emphasize joint movement within a null-space to provide the desired movement of a first set of joints. Methods may include calculating joint velocities that achieve the desired end effector movement using a pseudo-inverse solution and adjusting the calculated joint velocities using a potential function gradient within the joint space corresponding to the desired movement of the first set of joints. Methods may include use of a weighted pseudo-inverse solution and also an augmented Jacobian solution.

(Continued)

One or more auxiliary movements may also be provided using joint velocities calculated from the pseudo-inverse solution. Various configurations for systems utilizing such methods are provided herein.

20 Claims, 20 Drawing Sheets

Related U.S. Application Data

(60) Provisional application No. 61/800,924, filed on Mar. 15, 2013.

(51) Int. Cl.
| | |
|---|---|
| *A61B 34/37* | (2016.01) |
| *A61B 34/00* | (2016.01) |
| *A61B 1/00* | (2006.01) |
| *A61B 18/14* | (2006.01) |
| *B25J 9/16* | (2006.01) |
| *B25J 18/00* | (2006.01) |
| *A61B 18/00* | (2006.01) |

(52) U.S. Cl.
CPC ............. *A61B 34/25* (2016.02); *B25J 9/1607* (2013.01); *B25J 18/007* (2013.01); *A61B 2018/00595* (2013.01)

(58) Field of Classification Search
CPC ............... A61B 34/77; A61B 18/1445; A61B 2017/00075; A61B 17/00; A61B 17/062; A61B 17/1624; B25J 3/00; B25J 18/007; B25J 13/00; B25J 9/162
See application file for complete search history.

(56) References Cited

U.S. PATENT DOCUMENTS

| | | | |
|---|---|---|---|
| 6,493,608 B1 | 12/2002 | Niemeyer | |
| 9,468,501 B2* | 10/2016 | Hourtash | ............... B25J 9/1607 |
| 2007/0013336 A1 | 1/2007 | Nowlin et al. | |
| 2007/0151389 A1 | 7/2007 | Prisco et al. | |
| 2010/0331855 A1 | 12/2010 | Zhao et al. | |
| 2012/0150154 A1 | 6/2012 | Brisson et al. | |
| 2012/0245736 A1* | 9/2012 | Bosscher | ............... B25J 9/1607 700/263 |
| 2013/0105552 A1 | 5/2013 | Weir et al. | |
| 2013/0231680 A1 | 9/2013 | Diolaiti et al. | |
| 2013/0325029 A1 | 12/2013 | Hourtash et al. | |
| 2013/0325030 A1 | 12/2013 | Hourtash et al. | |
| 2014/0051987 A1 | 2/2014 | Kowshik et al. | |
| 2014/0052151 A1 | 2/2014 | Hingwe et al. | |
| 2014/0052152 A1 | 2/2014 | Au et al. | |
| 2014/0052153 A1 | 2/2014 | Griffiths et al. | |
| 2014/0052154 A1 | 2/2014 | Griffiths et al. | |
| 2014/0052155 A1 | 2/2014 | Hourtash et al. | |
| 2014/0052298 A1 | 2/2014 | Hourtash et al. | |
| 2014/0163736 A1 | 6/2014 | Azizian et al. | |
| 2014/0222207 A1 | 8/2014 | Bowling et al. | |
| 2014/0276950 A1 | 9/2014 | Smaby et al. | |
| 2014/0276951 A1 | 9/2014 | Hourtash et al. | |
| 2014/0276952 A1 | 9/2014 | Hourtash et al. | |
| 2014/0276953 A1 | 9/2014 | Swarup et al. | |
| 2014/0276954 A1 | 9/2014 | Hourtash | |
| 2014/0316430 A1 | 10/2014 | Hourtash et al. | |
| 2014/0316431 A1* | 10/2014 | Hourtash | ............... B25J 9/1607 606/130 |
| 2014/0358161 A1 | 12/2014 | Hourtash et al. | |
| 2015/0257840 A1 | 9/2015 | Mohr et al. | |
| 2015/0374446 A1 | 12/2015 | Malackowski et al. | |
| 2016/0030119 A1 | 2/2016 | Devengenzo et al. | |
| 2017/0172680 A1* | 6/2017 | Bowling | ................ A61B 34/74 |
| 2017/0173788 A1* | 6/2017 | Diolaiti | .................... B25J 9/161 |

FOREIGN PATENT DOCUMENTS

| | | |
|---|---|---|
| WO | WO-2006124390 A2 | 11/2006 |
| WO | WO-2013078529 A1 | 6/2013 |
| WO | WO-2014146120 A1 | 9/2014 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

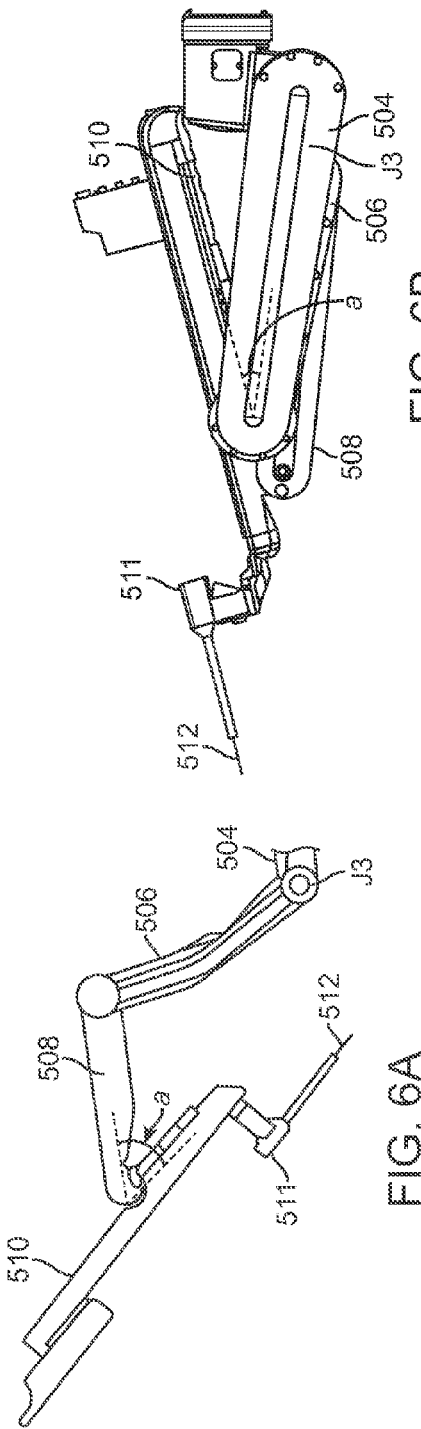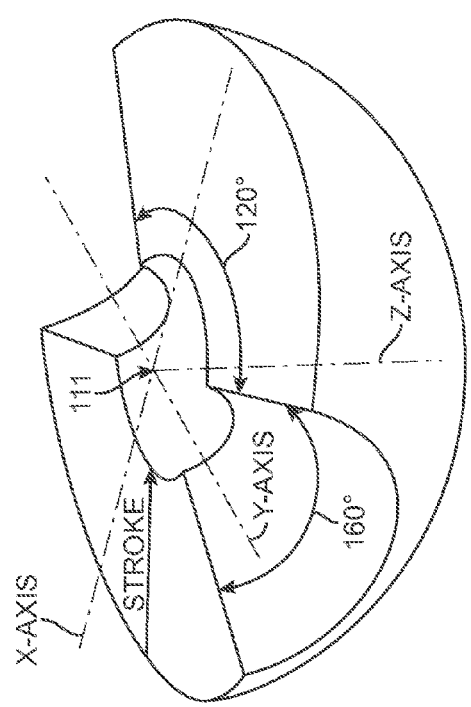
FIG. 6A  FIG. 6B  FIG. 6C

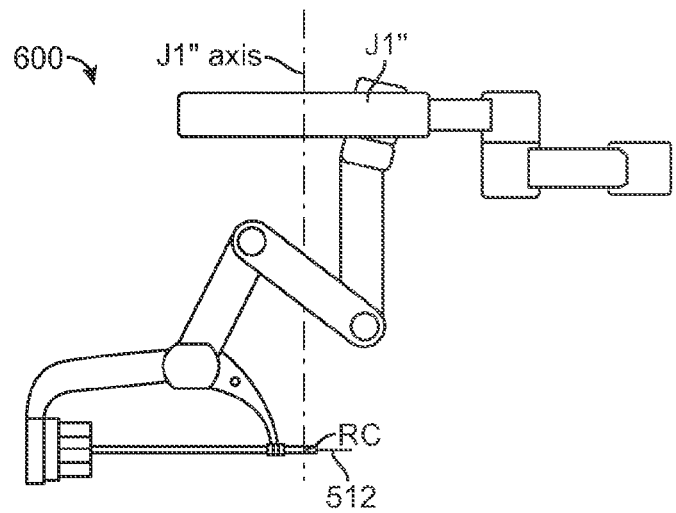
FIG. 12A
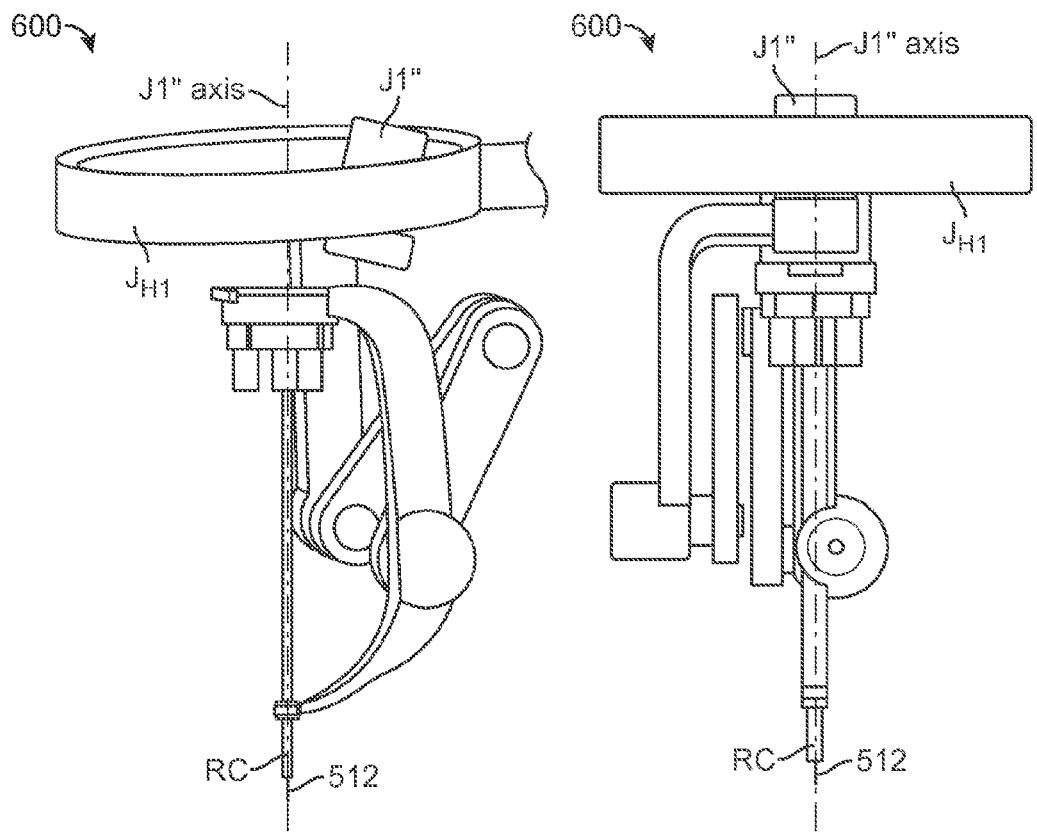
FIG. 12BFIG. 12C

SYSTEMS AND METHODS FOR USING THE NULL SPACE TO EMPHASIZE MANIPULATOR JOINT MOTION ANISOTROPICALLY

CROSS-REFERENCES TO RELATED APPLICATIONS

This application is a continuation of and claims the benefit of priority under 35 U.S.C. § 120 to U.S. patent application Ser. No. 14/218,842, filed on Mar. 18, 2014, which is a Non-Provisional of and claims the benefit of priority from U.S. Provisional Patent Application No. 61/800,924 filed on Mar. 15, 2013 and entitled "Systems and Methods for Using the Null Space to Emphasize Manipulator Joint Motion Anisotropically", the full disclosure of each of which is incorporated herein by reference.

The present application is generally related to the following commonly-owned applications: U.S. application Ser. No. 12/494,695 filed Jun. 30, 2009, entitled "Control of Medical Robotic System Manipulator About Kinematic Singularities;" U.S. application Ser. No. 12/406,004 filed Mar. 17, 2009, entitled "Master Controller Having Redundant Degrees of Freedom and Added Forces to Create Internal Motion;" U.S. application Ser. No. 11/133,423 filed May 19, 2005 (U.S. Pat. No. 8,004,229), entitled "Software Center and Highly Configurable Robotic Systems for Surgery and Other Uses;" U.S. application Ser. No. 10/957,077 filed Sep. 30, 2004 (U.S. Pat. No. 7,594,912), entitled "Offset Remote Center Manipulator For Robotic Surgery;" and U.S. application Ser. No. 09/398,507 filed Sep. 17, 1999 (U.S. Pat. No. 6,714,839), entitled "Master Having Redundant Degrees of Freedom;" U.S. Provisional Application No. 61/654,755 filed Jun. 1, 2012, entitled "Manipulator Arm-to-Patient Collision Avoidance Using a Null-Space;" and U.S. Provisional Application No. 61/654,773 filed Jun. 1, 2012, entitled "System and Methods for Avoiding Collisions Between Manipulator Arms Using a Null-Space," the disclosures of which are incorporated herein by reference in their entireties.

BACKGROUND OF THE INVENTION

The present invention generally provides improved surgical and/or robotic devices, systems, and methods.

Minimally invasive medical techniques are aimed at reducing the amount of tissue which is damaged during diagnostic or surgical procedures, thereby reducing patient recovery time, discomfort, and deleterious side effects. Millions of "open" or traditional surgeries are performed each year in the United States; many of these surgeries can potentially be performed in a minimally invasive manner. However, only a relatively small number of surgeries currently use minimally invasive techniques due to limitations in surgical instruments, and techniques, and the additional surgical training required to master them.

Minimally invasive telesurgical systems for use in surgery are being developed to increase a surgeon's dexterity as well as to allow a surgeon to operate on a patient from a remote location. Telesurgery is a general term for surgical systems where the surgeon uses some form of remote control, e.g., a servomechanism, or the like, to manipulate surgical instrument movements rather than directly holding and moving the instruments by hand. In such a telesurgery system, the surgeon is provided with an image of the surgical site at the remote location. While viewing typically a three-dimensional image of the surgical site on a suitable viewer or display, the surgeon performs the surgical procedures on the patient by manipulating master control input devices, which in turn controls the motion of robotic instruments. The robotic surgical instruments can be inserted through small, minimally invasive surgical apertures to treat tissues at surgical sites within the patient, often avoiding the trauma associated with accessing for open surgery. These robotic systems can move the working ends of the surgical instruments with sufficient dexterity to perform quite intricate surgical tasks, such as by pivoting shafts of the instruments at the minimally invasive aperture, sliding of the shaft axially through the aperture, rotating of the shaft within the aperture, and/or the like.

The servomechanism used for telesurgery will often accept input from two master controllers (one for each of the surgeon's hands) and may include two or more robotic arms or manipulators. Mapping of the hand movements to the image of the robotic instruments displayed by the image capture device can help provide the surgeon with accurate control over the instruments associated with each hand. In many surgical robotic systems, one or more additional robotic manipulator arms are included for moving an endoscope or other image capture device, additional surgical instruments, or the like.

A variety of structural arrangements can be used to support the surgical instrument at the surgical site during robotic surgery. The driven linkage or "slave" is often called a robotic surgical manipulator, and example as a robotic surgical manipulator during minimally invasive robotic surgery are described in U.S. Pat. Nos. 6,758,843; 6,246,200; and 5,800,423, the full disclosures of which are incorporated herein by reference. These linkages often make use of a parallelogram arrangement to hold an instrument having a shaft. Such a manipulator structure can constrain movement of the instrument so that the instrument shaft pivots about a remote center of spherical rotation positioned in space along the length of the rigid shaft. By aligning this center of rotation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially dangerous forces against the abdominal wall. Alternative manipulator structures are described, for example, in U.S. Pat. Nos. 6,702,805; 6,676,669; 5,855,583; 5,808,665; 5,445,166; and 5,184,601, the full disclosures of which are incorporated herein by reference.

While the new robotic surgical systems and devices have proven highly effective and advantageous, still further improvements would be desirable. For example, a manipulator arm may include additional redundant joints to provide increased movements or configurations under certain conditions. When moving surgical instruments within a minimally invasive surgical site, however, these joints may exhibit a significant amount of movement outside the patient, often more movement than needed or expected, particularly when pivoting instruments about minimally invasive apertures through large angular ranges. Alternative manipulator structures have been proposed which employ software control over joints of a highly configurable kinematic manipulator to restrain pivotal motion at the insertion site while inhibiting inadvertent manipulator/manipulator contact outside the patient (or the like). These highly configurable "software center" surgical manipulator systems may provide significant advantages, but may also present challenges. In particular, the mechanically constrained remote-center linkages may offer safety advantages in some conditions. Additionally, the wide range of configurations of the numerous joints often included in these manipulators may result in the manipulators being difficult to manually set-up in a configuration that is desirable for a particular procedure. As the range of surgeries being performed using telesurgical systems continues to expand, there is an increasing demand for expanding the available configurations and the range of motion of the instruments within the patient. Unfortunately, both of these changes can increase the challenges associated with the motion of the manipulators outside the body, and further increase the importance of avoiding unnecessary movement of the manipulators arm for certain tasks.

For these and other reasons, it would be advantageous to provide improved devices, systems, and methods for surgery, robotic surgery, and other robotic applications. It would be particularly beneficial if these improved technologies provided the ability to limit the amount of movement of the manipulator arm during certain tasks. Additionally, it would be desirable to provide such improvements while increasing the range of motion of the instruments for at least some tasks and without significantly increasing the size, mechanical complexity, or costs of these systems, and while maintaining or improving their dexterity.

BRIEF SUMMARY OF THE INVENTION

The present invention generally provides improved robotic and/or surgical devices, systems, and methods. In many embodiments, the invention will employ highly configurable surgical robotic manipulators. These manipulators, for example, may have more degrees of freedom of movement than the associated surgical end effectors have within a surgical workspace. A robotic surgical system in accordance with the present invention typically includes a manipulator arm supporting a robotic surgical instrument and a processor to calculate coordinated joint movements for manipulating an end effector of the instrument. The joints of the robotic manipulators supporting the end effectors allow the manipulator to move throughout a range of different configurations for a given end effector position and/or a given pivot point location. A manipulator may include additional redundant joints to allow for various types of auxiliary movements, such as a reconfiguration movement in response to a user command or another type of movement, such as a collision avoidance movement.

In one aspect, the invention allows for emphasis of motion of one or more joints of the manipulator within a null-space anisotropically so as to provide a desired movement of the one or more joints of the manipulator outside the body while effecting a desired end effector movement in response to a user input end effector manipulation command. The emphasis of the joint motion may be considered "anisotropic" since it is dependent on the direction of the joints, the emphasis extending within a null-space of the joints perpendicular to the movement of the joints that effect the desired end effector manipulation movement. The desired movement of the one or more joints, referred to herein as a first set of joints, may include a joint state, a combination of joint states, a relative joint state, a range of joints states, a profile of joint states, or any combination thereof. For example, the desired movement may include maintaining relatively uniform joint velocities between joints of the first set of joints, limiting joint velocities within a desired range, and/or maintaining a combination of joints states corresponding to a desired pose or collision-inhibiting configuration of the manipulator.

In general, commanded movement of the manipulator arm to effect a desired movement of the distal end effector utilizes movement of all joints of the manipulator arm. However, in some manipulators, particularly a highly configurable manipulator arm having redundant degrees of freedom, the velocities of certain joints or the total kinetic energy of the manipulator may exceed desirable levels. By emphasizing the motion of a first set of joints within a null-space direction, as determined by the calculated movement of the plurality of joints within a null-perpendicular space to effect a desired end effector movement, the invention provides the desired movement of the first set of joints during the desired end effector movement as detailed herein. Additionally, it may be advantageous to incorporate additional auxiliary movements to effect certain other tasks, such as a commanded reconfiguration movement or a collision avoidance movement of the manipulator arm.

In accordance with some embodiments, the invention includes: providing a manipulator arm including a movable distal surgical end effector, a proximal portion coupled to a base, and a plurality of joints between the distal portion and the base, the plurality of joints having sufficient degrees of freedom to allow a range of differing joint states for a given end effector state; receiving a manipulation command to move the end effector with a desired end effector movement; determining weighted joint velocities by calculating joint velocities within a null-perpendicular-space of a Jacobian matrix and adjusting the calculated joint velocities within a null-space of the Jacobian by applying a weighting within a joint space of the plurality of joints, the weighting corresponding to a desired movement for a first set of joints of the plurality of joints; and driving the joints according to the weighted joint velocities so as to effect the desired end effector movement and the desired movement of the first set of joints. The first set of joints may include one or more joints of the plurality of joints. The desired movement of the first set may include, but is not limited to: a joint state, a combination of joints states, a relative joint state, a range of joint states, a profile of joint states, or any combination thereof. In some embodiments, the method may further include: determining an end effector displacing movement of the plurality of joints to effect the desired end effector movement by calculating joint velocities within a null-perpendicular-space of a Jacobian matrix for the plurality of joints that achieve the desired end effector movement from which the weighted joint velocities are calculated, such that the unweighted calculated joint velocities remain available for use in various other auxiliary tasks, such as commanded reconfiguration or collision-avoidance movements.

In one aspect, determining the weighted joint velocities applies a weighted pseudo-inverse of the Jacobian to the calculated joint velocities. The weighting may be a weighting matrix in the joint space. The weighting may include a quadratic surface within the joint space, such as a parabaloid. In some embodiments, determining the end effector movement comprises calculating a pseudo-inverse solution of the Jacobian and determining the weighted joint velocities by calculating a difference between the pseudo-inverse solution and a potential function gradient of the pseudo-inverse solution and projecting the difference onto the null-space of the Jacobian to determine a null-space vector of the respective joints velocities.

In another aspect, any of the methods described herein may include: determining one or more auxiliary movements of the plurality of joints using the calculated joint velocities, and driving the joints according to the calculated auxiliary movement while maintaining a desired state of the end effector. The one or more auxiliary movements may include a desired movement of a second set of joints of the plurality of joints. The second set of joints may include one or more joints that may include one or more joints within the first set of joints. The one or more auxiliary movement may include: a commanded reconfiguration movement, a collision avoidance movement, an auxiliary task, or any combination thereof.

In one aspect of the present invention, a redundant degrees of freedom (RDOF) surgical robotic system with manipulation input is provided. The RDOF surgical robotic system comprises a manipulator assembly, one or more user input devices, and a processor with a controller. A manipulator arm of the assembly has a plurality of joints providing sufficient degrees of freedom that allow a range of joint states for a given end effector state. Typically, in response to receiving a manipulation command to move the end effector with a desired movement, the system calculates end effector displacing movement of the joints by calculating joint velocities within a null-perpendicular-space of the Jacobian orthogonal to the null-space, and drives the joints according to the calculated movement to effect the desired end effector movement. To enlarge the manipulator's work space or to allow various auxiliary tasks, the system may include a revolute proximal most joint of the manipulator arm and/or a distal revolute joint coupling an instrument to a proximal portion of the manipulator arm.

In another aspect, the manipulator is configured to move such that an intermediate portion of the instrument shaft pivots about a remote center. Between the manipulator and the instrument, there are a plurality of driven joints providing sufficient degrees of freedom to allow a range of joint states for an end effector position when the intermediate portion of the instrument shaft passes through an access site. A processor having a controller couples the input device to the manipulator. In response to receiving a manipulation command to effect a desired end effector's movement, the system calculates end effector displacing movement of the joints, comprising calculating joint velocities within a null-perpendicular-space of the Jacobian orthogonal to the null-space. The processor is further configured to calculate weighted joint velocities by adjusting the calculated joint velocities by applying a weighting within a joint space of the plurality of joints to effect a desired movement for a first set of joints of the plurality of joints and transmit a command to the manipulator arm in response to the end effector displacing movement to drive the manipulator arm with the calculated weighted joint velocities so as to effect the desired end effector movement and the desired movement of the first set of joints. The processor may be configured so that calculating weighted joint velocities uses a weighting matrix applied within the joint space or more particularly according to a quadratic surface, such as a paraboloid, the weighting corresponds to the desired movement of the first set of joints such that movement of the joints are emphasized along the null-perpendicular space to provide the desired movement of the first set of joints. In one aspect, the desired movement is movement of the first set of joints that approaches or approximates the movement corresponding to the weighting matrix or surface in the joint space.

In one aspect, the proximal portion of the manipulator arm is attached to the base such that movement of the proximal portion relative to the base is inhibited while the joints are driven. In another aspect, the proximal portion is coupled to the base by a joint such that the proximal portion of the manipulator arm is moveable relative to the base while the joints are driven. In an example embodiment, the joint coupling the proximal portion of the manipulator to the base is a revolute joint that supports the manipulator arm such that joint movement of the revolute joint pivots one or more joints of the manipulator arm about a pivotal axis of the revolute joints. In many embodiments, the pivotal axis of the revolute joint extends from the joints through a remote center about which an instrument shaft of the end effector pivots. In one aspect, movement of the revolute joint pivots one or more joints of the manipulator arm about a cone distally tapered and oriented towards the distal end effector, typically the remote center. The cone around which the manipulator arm pivots in this aspect, corresponds to a cone shaped void within the range of motion of the tool tip, in which the movement of the tool may be impossible or impaired, discussed in further detail below.

In another aspect, the joint coupling the proximal portion of the manipulator to the base is moveable relative to the base along a path, typically an arcuate or substantially circular path such that movement of the joint along the path pivots one or more joints of the manipulator arm about an axis extending through a distal portion of the manipulator arm near the instrument, preferably through a remote center about which the instrument shaft pivots. In some embodiments, the manipulator includes a revolute joint coupling the proximal portion of the manipulator to the base, the revolute joint being moveable relative to the base along a path, which may linear, arcuate or substantially circular.

In yet another aspect of the present invention, a surgical robotic manipulator with a proximal revolute joint and a distal parallelogram linkage is provided, the pivotal axis of the revolute joint substantially intersecting with the axis of the instrument shaft of the end effector, preferably at a remote center if applicable. The system further includes a processor having a controller coupling the input to the manipulator arm and configured to calculate a movement of the plurality of joints in response to a user input command by calculating weighted joint velocities that effect the desired end effector movement, the weighting of the joint velocities corresponding to a desired movement of one or more of the joints between the proximal base and end effector. In some embodiments, the processor is further configured to calculate joint velocities within the null-space from the unweighted joint velocities to effect one or more auxiliary tasks.

A further understanding of the nature and advantages of the present invention will become apparent by reference to the remaining portions of the specification and drawings.

BRIEF DESCRIPTION OF THE DRAWINGS

FIGS. 6A-6B show an example manipulator arm in the pitch forward configuration and pitch back configurations, respectively.

FIG. 6C; shows a graphical representation of the range of motion of the surgical instrument tool tip of an example manipulator arm, including a cone of silence or conical tool access limit zone in each of the pitch forward and pitch back configurations.

FIGS. 12A-12C show exemplary manipulator arms having a proximal joint that translates a proximal joint supporting the manipulator arm about a path of the joint.

DETAILED DESCRIPTION OF THE INVENTION

Figure 1A:
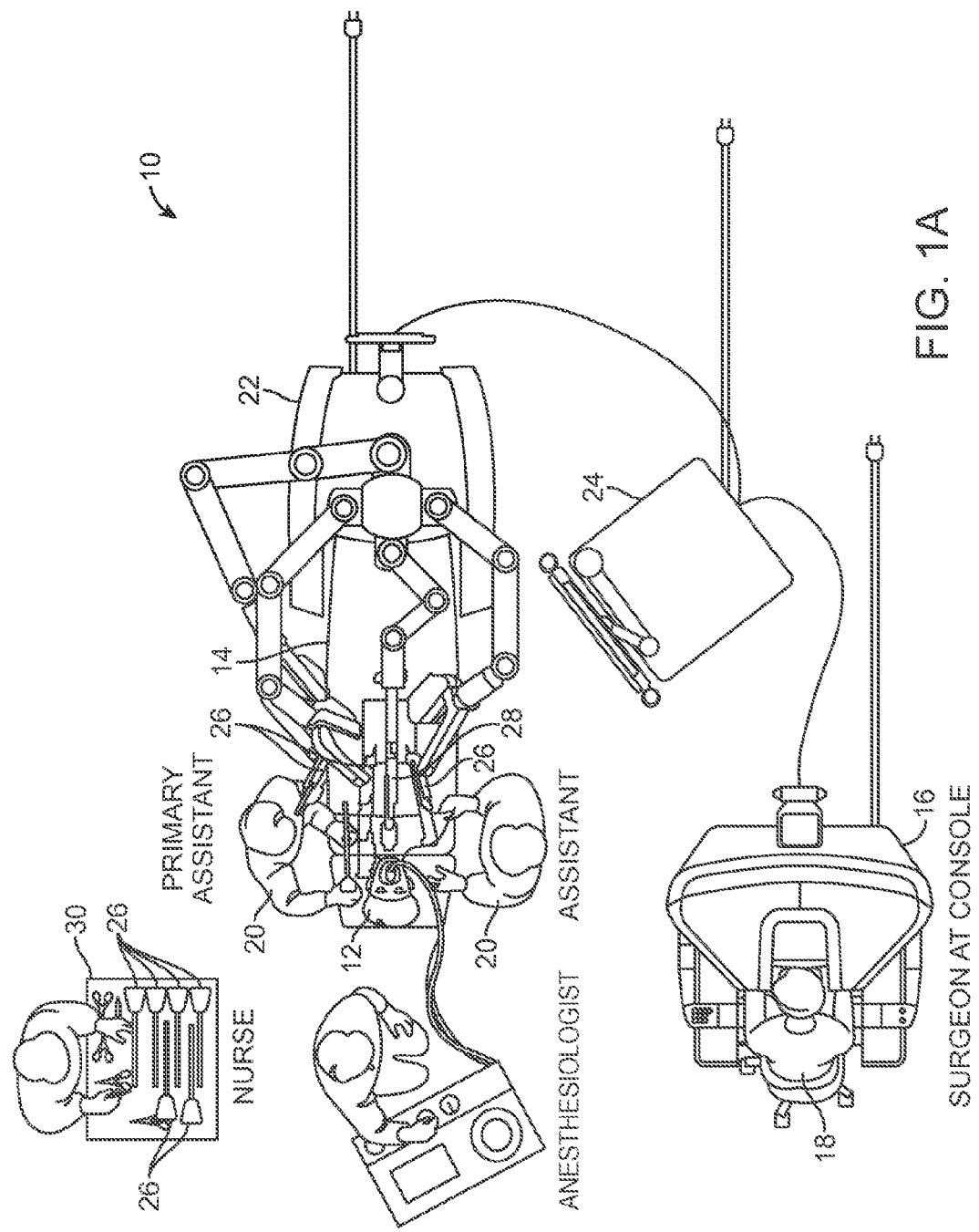
FIG. 1A is an overhead view of a robotic surgical system in accordance with embodiments of the present invention, the robotic surgical system having a surgical station with a plurality of robotic manipulators for robotically moving surgical instruments having surgical end effectors at an internal surgical site within a patient.

The present invention generally provides improved surgical and robotic devices, systems, and methods. The invention is particularly advantageous for use with surgical robotic systems in which a plurality of surgical tools or instruments will be mounted on and moved by an associated plurality of robotic manipulators during a surgical procedure. The robotic systems will often comprise telerobotic, telesurgical, and/or telepresence systems that include processors configured as master-slave controllers. By providing robotic systems employing processors appropriately configured to move manipulator assemblies with articulated linkages having relatively large numbers of degrees of freedom, the motion of the linkages can be tailored for work through a minimally invasive access site. While aspects of the invention are generally described manipulators having redundant degrees of freedom, it is appreciated that aspects may apply to non-redundant manipulators, for example a manipulator experiencing or approaching a singularity.

The robotic manipulator assemblies described herein will often include a robotic manipulator and a tool mounted thereon (the tool often comprising a surgical instrument in surgical versions), although the term "robotic assembly" will also encompass the manipulator without the tool mounted thereon. The term "tool" encompasses both general or industrial robotic tools and specialized robotic surgical instruments, with these later structures often including an end effector which is suitable for manipulation of tissue, treatment of tissue, imaging of tissue, or the like. The tool/manipulator interface will often be a quick disconnect tool holder or coupling, allowing rapid removal and replacement of the tool with an alternate tool. The manipulator assembly will often have a base which is fixed in space during at least a portion of a robotic procedure, and the manipulator assembly may include a number of degrees of freedom between the base and an end effector of the tool. Actuation of the end effector (such as opening or closing of the jaws of a gripping device, energizing an electrosurgical paddle, or the like) will often be separate from, and in addition to, these manipulator assembly degrees of freedom.

The end effector will typically move in the workspace with between two and six degrees of freedom. As used herein, the term "position" encompasses both location and orientation. Hence, a change in a position of an end effector (for example) may involve a translation of the end effector from a first location to a second location, a rotation of the end effector from a first orientation to a second orientation, or a combination of both. When used for minimally invasive robotic surgery, movement of the manipulator assembly may be controlled by a processor of the system so that a shaft or intermediate portion of the tool or instrument is constrained to a safe motion through a minimally invasive surgical access site or other aperture. Such motion may include, for example, axial insertion of the shaft through the aperture site into a surgical workspace, rotation of the shaft about its axis, and pivotal motion of the shaft about a pivot point adjacent the access site.

Many of the example manipulator assemblies described herein have more degrees of freedom than are needed to position and move an end effector within a surgical site. For example, a surgical end effector that can be positioned with six degrees of freedom at an internal surgical site through a minimally invasive aperture may in some embodiments have nine degrees of freedom (six end effector degrees of freedom—three for location, and three for orientation—plus three degrees of freedom to comply with the access site constraints), but will often have ten or more degrees of freedom. Highly configurable manipulator assemblies having more degrees of freedom than are needed for a given end effector position can be described as having or providing sufficient degrees of freedom to allow a range of joint states for an end effector position in a workspace. For example, for a given end effector position, the manipulator assembly may occupy (and be driven between) any of a range of alternative manipulator linkage positions. Similarly, for a given end effector velocity vector, the manipulator assembly may have a range of differing joint movement speeds for the various joints of the manipulator assembly within the null-space of the Jacobian.

The invention provides robotic linkage structures which are particularly well suited for surgical (and other) applications in which a wide range of motion is desired, and for which a limited dedicated volume is available due to the presence of other robotic linkages, surgical personnel and equipment, and the like. The large range of motion and reduced volume needed for each robotic linkage may also provide greater flexibility between the location of the robotic support structure and the surgical or other workspace, thereby facilitating and expediting setup.

The term "state" of a joint or the like will often herein refer to the control variables associated with the joint. For example, the state of an angular joint can refer to the angle defined by that joint within its range of motion, and/or to the angular velocity of the joint. Similarly, the state of an axial or prismatic joint may refer to the joint's axial position, and/or to its axial velocity. While many of the controllers described herein comprise velocity controllers, they often also have some position control aspects. Alternative embodiments may rely primarily or entirely on position controllers, acceleration controllers, or the like. Many aspects of control system that can be used in such devices are more fully described in U.S. Pat. No. 6,699,177, the full disclosure of which is incorporated herein by reference. Hence, so long as the movements described are based on the associated calculations, the calculations of movements of the joints and movements of an end effector described herein may be performed using a position control algorithm, a velocity control algorithm, a combination of both, and/or the like.

In certain aspects, the tool of an exemplary manipulator arm pivots about a pivot point adjacent a minimally invasive aperture. In some embodiments, the system may utilize a hardware remote center, such as the remote center kinematics described in U.S. Pat. No. 6,786,896, the entire contents of which are incorporated herein by reference. Such systems may utilize a double parallelogram linkage which constrains the movement of the linkages such that the shaft of the instrument supported by the manipulator pivots about a remote center point. Alternative mechanically constrained remote center linkage systems are known and/or may be developed in the future. Surprisingly, work in connection with the present invention indicates that remote center linkage systems may benefit from highly configurable kinematic architectures. In particular when a surgical robotic system has a linkage that allows pivotal motion about two axes intersecting at or near a minimally invasive surgical access site, the spherical pivotal motion may encompass the full extent of a desired range of motion within the patient, but may still suffer from avoidable deficiencies (such as being poorly conditioned, being susceptible to arm-to-arm or arm-to-patient contact outside the patient, and/or the like). At first, adding one or more additional degrees of freedom that are also mechanically constrained to pivotal motion at or near the access site may appear to offer few or any improvements in the range of motion. Nonetheless, surprisingly, such joints can provide significant advantages by allowing the overall system to be configured in or driven toward a collision-inhibiting pose, by further extending the range of motion for other surgical procedures, and the like. In other embodiments, the system may utilize software to achieve a remote center, such as described in U.S. Pat. No. 8,004,229, the entire contents of which are incorporated herein by reference. In a system having a software remote center, the processor calculates movement of the joints so as to pivot an intermediate portion of the instrument shaft about a pivot point determined, as opposed to a mechanical constraint. By having the capability to compute software pivot points, different modes characterized by the compliance or stiffness of the system can be selectively implemented. More particularly, different system modes over a range of pivot points/centers (e.g., moveable pivot points, passive pivot points, fixed/rigid pivot point, soft pivot points) can be implemented as desired.

Despite the many advantages of a robotic surgical system having multiple highly configurable manipulators, since the manipulators include a relatively large number of joints and links between the base and instrument with redundant degrees of freedom, the commanded motion of the plurality of joints to achieve a desired movement of a distal end effector and/or the remote center may produce joint velocities that are undesirable, excessive kinetic energy associated with one or more joints, or may produce motion that does not meet a desired motion preference. Examples of undesirable joint velocities may include an undesirable combination of joint states, excessive joint velocities for one or more joints, or disproportional joint states. The present invention provides a desired movement, such as a combination of joint states or other such movements described herein, for one or more joints during commanded end effector movement.

In one aspect, the system is configured to calculate weighted joint velocities that achieve the commanded movement of a tool tip and/or remote center. The joint velocities are weighted in a joint space to emphasize motion of the joints anisotropically in a null-space direction, the weighting corresponding to a desired state or movement of a first set of joints, such that driving the joints according to the weighted joint velocities achieves the commanded movement while providing the desired movement of the first set of joints. In a first approach, weighted joint velocities are calculated by applying a weighting matrix within the joint space. In a second approach, unweighted joint velocities that achieve the commanded movement of the tool tip and/or remote center and weighted joint velocities are calculated using the unweighted joint velocities. This approach is particularly useful as the unweighted joint velocities can be used to effect one or more various other tasks, such as commanded reconfiguration and collision avoidance tasks. In certain aspects, the unweighted and weighted joint velocities are calculated within the same kernel using a weighting comprising a quadratic surface within the joint space, such as a paraboloid or ellipsoid. The weighted joint velocities can be calculated from unweighted joint velocities using the difference between the pseudo-inverse solution and a potential function gradient of the solution, as described for example in further detail below.

In one aspect, a commanded end effector movement within a surgical space is effected by driving one or more joints of the manipulator according to a coordinated end effector displacing movement of the joints calculated by a processor within a null-space-perpendicular of the kinematic Jacobian. Various other tasks, such as a reconfiguration movement or a collision avoidance movement, may be effected while maintaining the desired state of the end effector by driving one or more joints of the manipulator according to coordinated movement of the joints calculated within a null-space of the Jacobian, often concurrent with the end effector displacing movement. In some embodiments, these various other tasks may utilize unweighted joint velocities, such that the system can be configured to calculate both weighted and unweighted joint velocities within the same iteration or kernel. Such embodiments may utilize alternative methods to weight the joint velocities using the unweighted joint velocities so as to reduce the required calculations to determine the weighted joint velocities.

In some embodiments, calculated movement relating to various other tasks, such as an avoidance movement based on an autonomous algorithm, may overlay the calculated joint velocities to effect the various other tasks. Examples of such collision avoidance movements are described in U.S.

Provisional Application No. 61/654,755 filed Jun. 1, 2012, entitled "Manipulator Arm-to-Patient Collision Avoidance Using a Null-Space;" and U.S. Provisional Application No. 61/654,773 filed Jun. 1, 2012, entitled "Systemr and Methods for Avoiding Collisions Between Manipulator Arms Using a Null-Space," the disclosures of which are incorporated herein by reference in their entireties. The calculated movement that overlays the anisotropically emphasized joint movement, however, is not limited to autonomous movement and may include various other movements, such as a commanded reconfiguration movement, movement to improve a range of motion, dexterity or conditioning. Examples of such commanded reconfiguration are described in U.S. Provisional Application No. 61/654,764 filed Jun. 1, 2012, entitled "Commanded Reconfiguration of a Surgical Manipulator Using the Null-Space," the disclosure of which is incorporated herein by reference in its entirety.

In the following description, various embodiments of the present invention will be described. For purposes of explanation, specific configurations and details are set forth in order to provide a thorough understanding of the embodiments. However, it will also be apparent to one skilled in the art that the present invention may be practiced without various specific details. Furthermore, well-known features may be omitted or simplified in order not to obscure the embodiment being described.

Referring now to the drawings, in which like reference numerals represent like parts throughout the several views, FIG. 1A is an overhead view illustration of a Minimally Invasive Robotic Surgical (MIRS) system 10, in accordance with many embodiments, for use in performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 so as to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 1B:
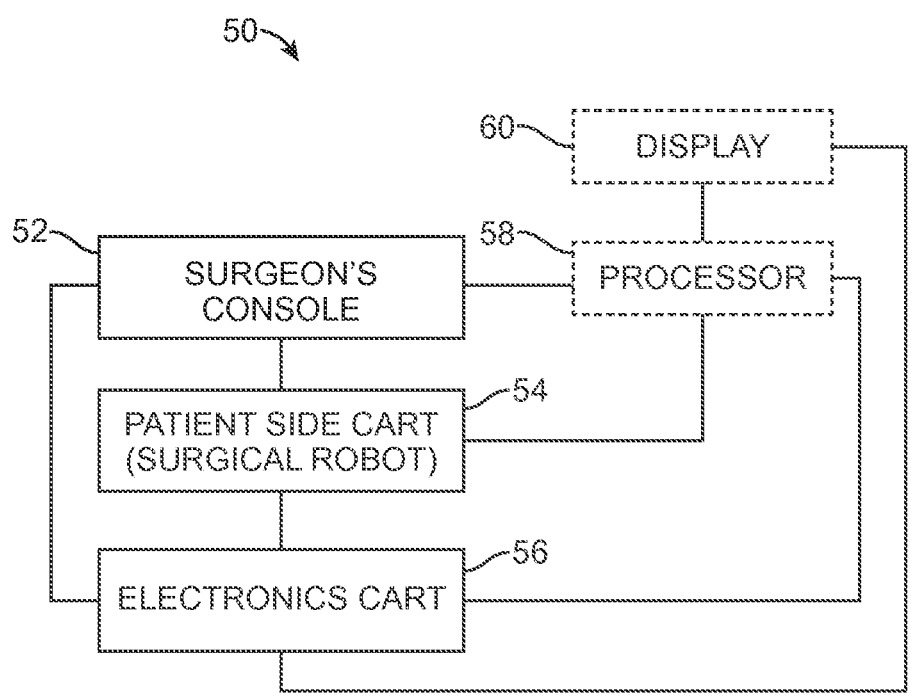
FIG. 1B diagrammatically illustrates the robotic surgical system of FIG. 1A.

FIG. 1B diagrammatically illustrates a robotic surgery system 50 (such as MIRS system 10 of FIG. 1A). As discussed above, a Surgeon's Console 52 (such as Surgeon's Console 16 in FIG. 1A) can be used by a Surgeon to control a Patient Side Cart (Surgical Robot) 54 (such as Patent Side Cart 22 in FIG. 1A) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1A). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, and can be used to process the captured images. The images can also be processed by a combination the Electronics Cart 56 and the processor 58, and can be coupled together so as to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 2:
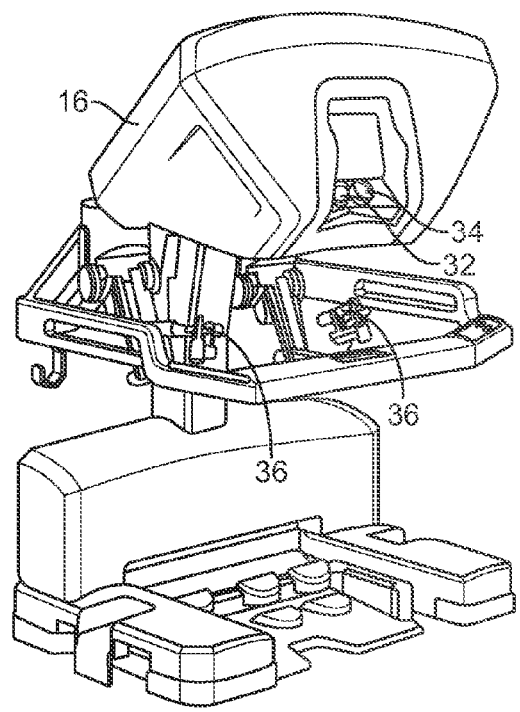
FIG. 2 is a perspective view illustrating a master surgeon console or workstation for inputting surgical procedure commands in the surgical system of FIG. 1A, the console including a processor for generating manipulator command signals in response to the input commands.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn causes the Patient Side Cart 22 (shown in FIG. 1A) to manipulate one or more tools. The input control devices 36 can provide the same degrees of freedom as their associated tools 26 (shown in FIG. 1A) so as to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
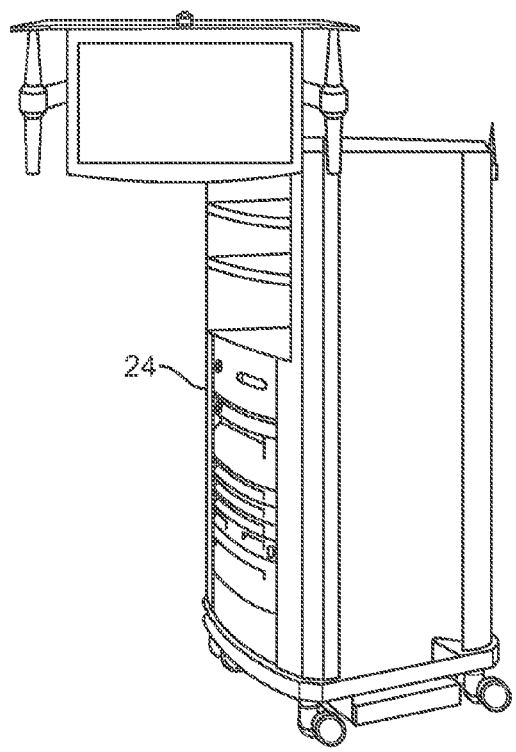
FIG. 3 is a perspective view of the electronics cart of FIG. 1A.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images so as to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters so as to compensate for imaging errors of the image capture device, such as optical aberrations.

Figure 4:
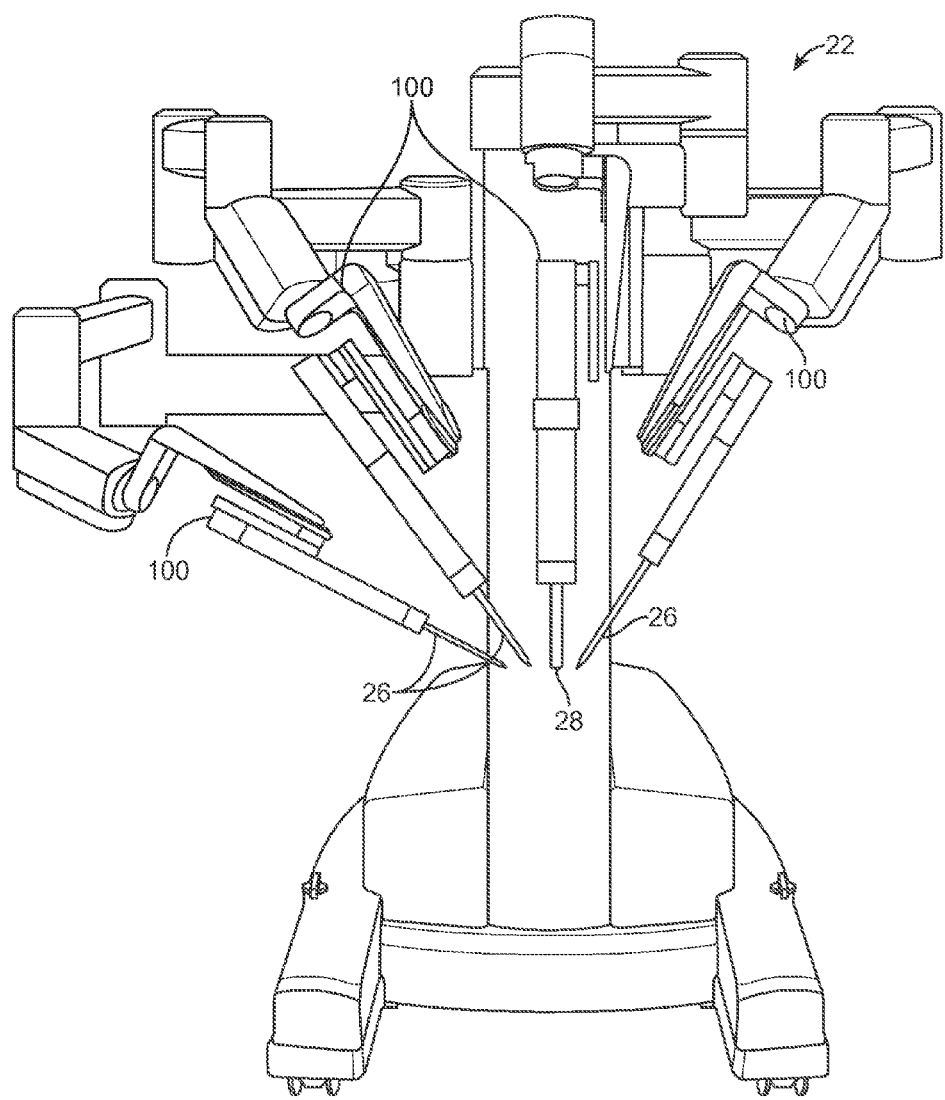
FIG. 4 is a perspective view of a patient side cart having four manipulator arms.

FIG. 4 shows a Patient Side Cart 22 having a plurality of manipulator arms, each supporting a surgical instrument or tool 26 at a distal end of the manipulator arm. The Patient Side Cart 22 shown includes four manipulator arms 100 which can be used to support either a surgical tool 26 or an imaging device 28, such as a stereoscopic endoscope used for the capture of images of the site of the procedure. Manipulation is provided by the robotic manipulator arms 100 having a number of robotic joints. The imaging device 28 and the surgical tools 26 can be positioned and manipulated through incisions in the patient so that a kinematic remote center is maintained at the incision so as to minimize the size of the incision. Images of the surgical site can include images of the distal ends of the surgical instruments or tools 26 when they are positioned within the field-of-view of the imaging device 28.

Regarding surgical tool 26, a variety of alternative robotic surgical tools or instruments of different types and differing end effectors may be used, with the instruments of at least some of the manipulators being removed and replaced during a surgical procedure. Several of these end effectors, including DeBakey Forceps, microforceps, Potts scissors, and clip applier include first and second end effector elements which pivot relative to each other so as to define a pair of end effector jaws. Other end effectors, including scalpel and electrocautery probe have a single end effector element. For instruments having end effector jaws, the jaws will often be actuated by squeezing the grip members of handle. Single end effector instruments may also be actuated by gripping of the grip members, for example, so as to energize an electrocautery probe.

The elongate shaft of instrument 26 allow the end effectors and the distal end of the shaft to be inserted distally into a surgical worksite through a minimally invasive aperture, often through an abdominal wall or the like. The surgical worksite may be insufflated, and movement of the end effectors within the patient will often be effected, at least in part, by pivoting of the instrument 26 about the location at which the shaft passes through the minimally invasive aperture. In other words, manipulators 100 will move the proximal housing of the instrument outside the patient so that shaft extends through a minimally invasive aperture location so as to help provide a desired movement of end effector. Hence, manipulators 100 will often undergo significant movement outside patient P during a surgical procedure.

Exemplary manipulator arms in accordance with many embodiments of the present invention can be understood with reference to FIGS. 5A-12C. As described above, a manipulator arm generally supports a distal instrument or surgical tool and effects movements of the instrument relative to a base. As a number of different instruments having differing end effectors may be sequentially mounted on each manipulator during a surgical procedure (typically with the help of a surgical assistant), a distal instrument holder will preferably allow rapid removal and replacement of the mounted instrument or tool. As can be understood with reference to FIG. 4, manipulators are proximally mounted to a base of the patient side cart. Typically, the manipulator arm includes a plurality of linkages and associated joints extending between the base and the distal instrument holder. In one aspect, an exemplary manipulator includes a plurality of joints having redundant degrees of freedom such that the joints of the manipulator arm can be driven into a range of differing configurations for a given end effector position. This may be the case for any of the embodiments of manipulator arms disclosed herein.

Figure 5A:
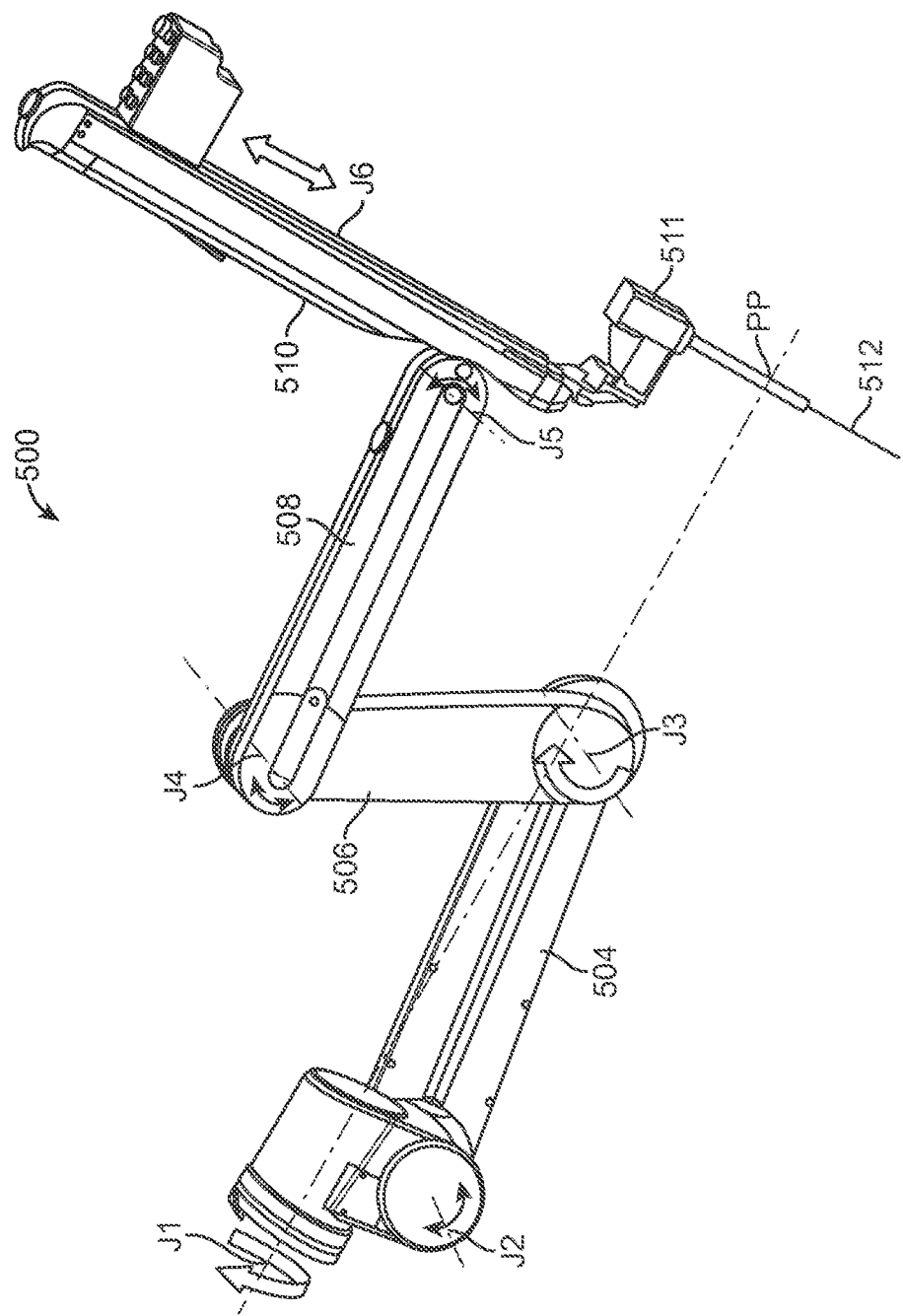
FIGS. 5A-5D show an example manipulator arm.

In many embodiments, such as shown for example in FIG. 5A, an exemplary manipulator arm includes a proximal revolute joint J1 that rotates about a first joint axis so as to revolve the manipulator arm distal of the joint about the joint axis. In some embodiments, revolute joint J1 is mounted directly to the base, while in other embodiments, joint J1 may be mounted to one or more movable linkages or joints. The joints of the manipulator, in combination, have redundant degrees of freedom such that the joints of the manipulator arm can be driven into a range of differing configurations for a given end effector position. For example, the manipulator arm of FIGS. 5A-5D may be maneuvered into differing configurations while the distal member 511 supported within the instrument holder 510 maintains a particular state and may include a given position or velocity of the end effector. Distal member 511 is typically a cannula through which the tool shaft 512 extends, and the instrument holder 510 is typically a carriage (shown as a brick-like structure that translates on a spar) to which the instrument attaches before extending through the cannula 511 into the body of the patient through the minimally invasive aperture.

Figure 5B:
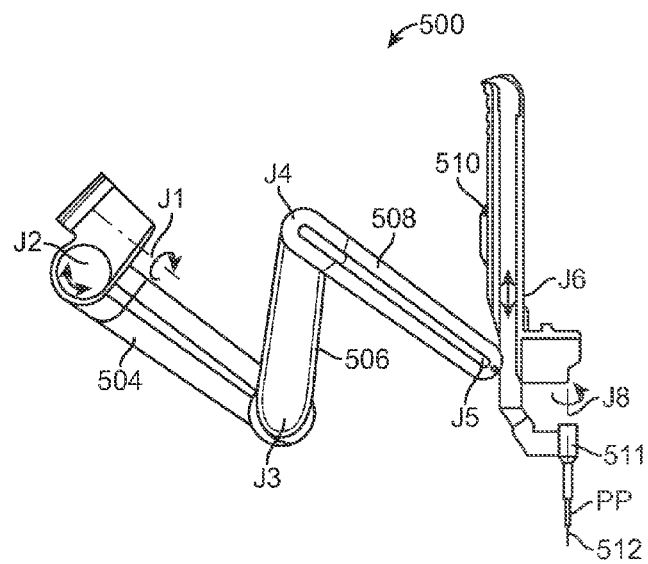
Figure 5D:
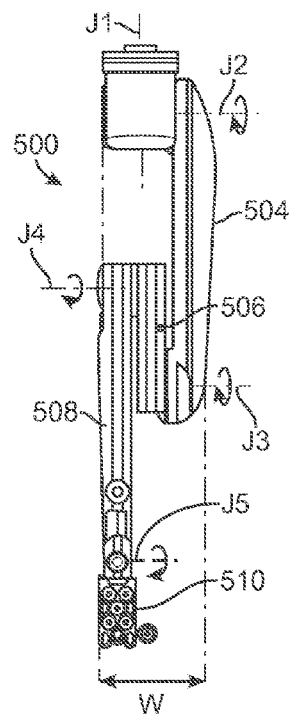
Figure 5C:
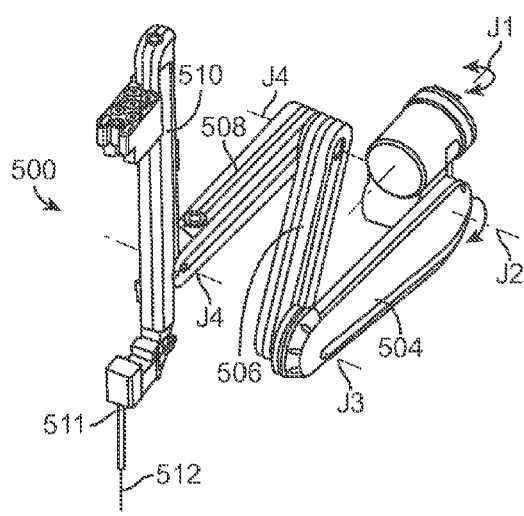

Describing the individual links of manipulator arm 500 of FIGS. 5A-5D along with the axes of rotation of the joints connecting the links as illustrated in FIG. 5A-5D, a first link 504 extends distally from a pivotal joint J2 which pivots about its joint axis and is coupled to revolute joint J1 which rotates about its joint axis. Many of the remainder of the joints can be identified by their associated rotational axes, as shown in FIG. 5A. For example, a distal end of first link 504 is coupled to a proximal end of a second link 506 at a pivotal joint J3 that pivots about its pivotal axis, and a proximal end of a third link 508 is coupled to the distal end of the second link 506 at a pivotal joint J4 that pivots about its axis, as shown. The distal end of the third link 508 is coupled to instrument holder 510 at pivotal joint J5. Typically, the pivotal axes of each of joints J2, J3, J4, and J5 are substantially parallel and the linkages appear "stacked" when positioned next to one another, as shown in FIG. 5D, so as to provide a reduced width w of the manipulator arm and improve patient clearance during maneuvering of the manipulator assembly. In many embodiments, the instrument holder also includes additional joints, such as a prismatic joint J6 that facilitates axial movement of instrument 306 through the minimally invasive aperture and facilitates attachment of the instrument holder to a cannula through which the instrument is slidably inserted.

The distal member or cannula 511 through which the tool 512 extends may include additional degrees of freedom distal of instrument holder 510. Actuation of the degrees of freedom of the instrument will often be driven by motors of the manipulator, and alternative embodiments may separate the instrument from the supporting manipulator structure at a quickly detachable instrument holder/instrument interface so that one or more joints shown here as being on the instrument are instead on the interface, or vice versa. In some embodiments, cannula 511 includes a rotational joint J7 (not shown) near or proximal of the insertion point of the tool tip or the pivot point PP, which generally is disposed at the site of a minimally invasive aperture. A distal wrist of the instrument allows pivotal motion of an end effector of surgical tool 512 about instrument joints axes of one or more joints at the instrument wrist. An angle between end effector jaw elements may be controlled independently of the end effector location and orientation.

The range of motion of an exemplary manipulator assembly can be appreciated by referring to FIGS. 6A-6C. During a surgical procedure, an exemplary manipulator arm can be maneuvered into a pitch forward configuration, as shown in FIG. 6A, or into a pitch back configuration, as shown in FIG. 6B, as needed to access particular patient tissues within a surgical workspace. A typical manipulator assembly includes an end effector that can pitch forwards and backwards about an axis by at least ±60 degrees, preferably by about ±75 degrees, and can also yaw about an axis by ±80 degrees. Although this aspect allows for increased maneuverability of the end effector with the assembly, there may be configurations in which movement of the end effector may be limited, particularly when the manipulator arm is in the full pitch forward or full pitch back configuration as in FIGS. 6A and 6B. In one embodiment, the manipulator arm has a Range of Motion (ROM) of (+/−75 deg) for the outer pitch, and (+/−300 degrees) for the outer yaw joints, respectively. In some embodiments, the ROM may be increased for the outer pitch to provide a ROM larger than (+/−90 deg) in which case a cone of space in which joint movement is limited or impossible could be made to disappear entirely, although generally the inner sphere associated with insertion limitations would remain. It is appreciated that various embodiments may be configured to have increased or decreased ROM, that the above noted ROMs are provided for illustrative purposes, and further that the invention is not limited to the ROMs described herein.

FIG. 6C graphically represents the overall range of motion and workspace of the tool tip of the exemplary manipulator of FIGS. 5A-5B. Although the workspace is shown as hemisphere, it may also be represented as a sphere depending on the range of motion and configuration of one or more revolute joints of the manipulator, such as joint J1. As shown, the hemisphere in FIG. 6C includes a central, small spherical void as well as two conical voids. The voids represent the areas in which movement of the tool tip may be impossible due to mechanical constraints or unfeasible due to extremely high joint velocities that make movement of the end effector difficult or slow. For these reasons, the conical void are referred to as the "cone of silence." In some embodiments, the manipulator arm may reach a singularity at a point within the cone. Since movement of the manipulator within or near the cone of silence may be impaired, it can be difficult to move the manipulator arm away from the cone of silence without manually moving one or more links of the manipulator to reconfigure the linkages and joints of the manipulator, which may require an alternative operating mode and delays the surgical procedure.

Movement of the instrument shaft into or near these conical portions typically occurs when the angle between distal linkages in the manipulator is relatively small. Thus, such configurations can be avoided by anisotropically emphasizing movement of the manipulator so as to increase the angles between linkages (so that the linkages are moved into a more orthogonal position relative to each other). For example, in the configurations shown in FIGS. 6A and 6B, when the angle between the distal most link and the instrument holder (angle a) becomes relatively small movement of the manipulator may become more difficult. Depending on the range of joint movements in the remaining joints in various embodiments, when the angle between certain linkages decreases, movement of the manipulator may be inhibited and in some cases, the manipulator arm may no longer be redundant. A manipulator configuration in which the instrument shaft nears these conical portions, or in which the angles between linkages are relatively low is said to be "poorly conditioned" such that maneuverability and dexterity of the manipulator arm is limited. It is desirable that the manipulator be "well conditioned" so as to maintain dexterity and range of movement. In one aspect, the present invention allows a user to avoid movement of the instrument shaft near the above described conical portions by simply entering a command to reconfigure the manipulator as desired, even during movement of the end effector in a surgical procedure. This aspect is particularly useful should the manipulator, for whatever reason, become "poorly conditioned."

While the embodiments of the manipulator described above may be utilized in the present invention, some embodiments may include additional joints, which may also be used to improve dexterity and the conditioning of the manipulator arm. For example, an exemplary manipulator may include a revolute joint and/or linkage proximal of joint J1 which can be used to revolve the manipulator arm of FIG. 5A, and its associated cone of silence, about an axis of the revolute joint so as to reduce or eliminate the cone of silence. In another embodiment, the exemplary manipulator may also include a distal pivotal joint that pivots the instrument holder about an axis substantially perpendicular to joint J5, thereby offsetting the tool tip so as to further reduce the cone of silence and improve the range of movement of the surgical tool. In still another embodiment, a proximal joint of the manipulator arm, such as J1, may be movably mounted on the base, so as to move or shift the cone of silence as needed and improve the range of motion of the manipulator tool tip. The use and advantages of such additional joints can be understood by referring to FIGS. 7A-12C, which illustrate examples of such joints, which may each be used independent of one another or used in combination, in any of the exemplary manipulator arms described herein.

Figure 7A:
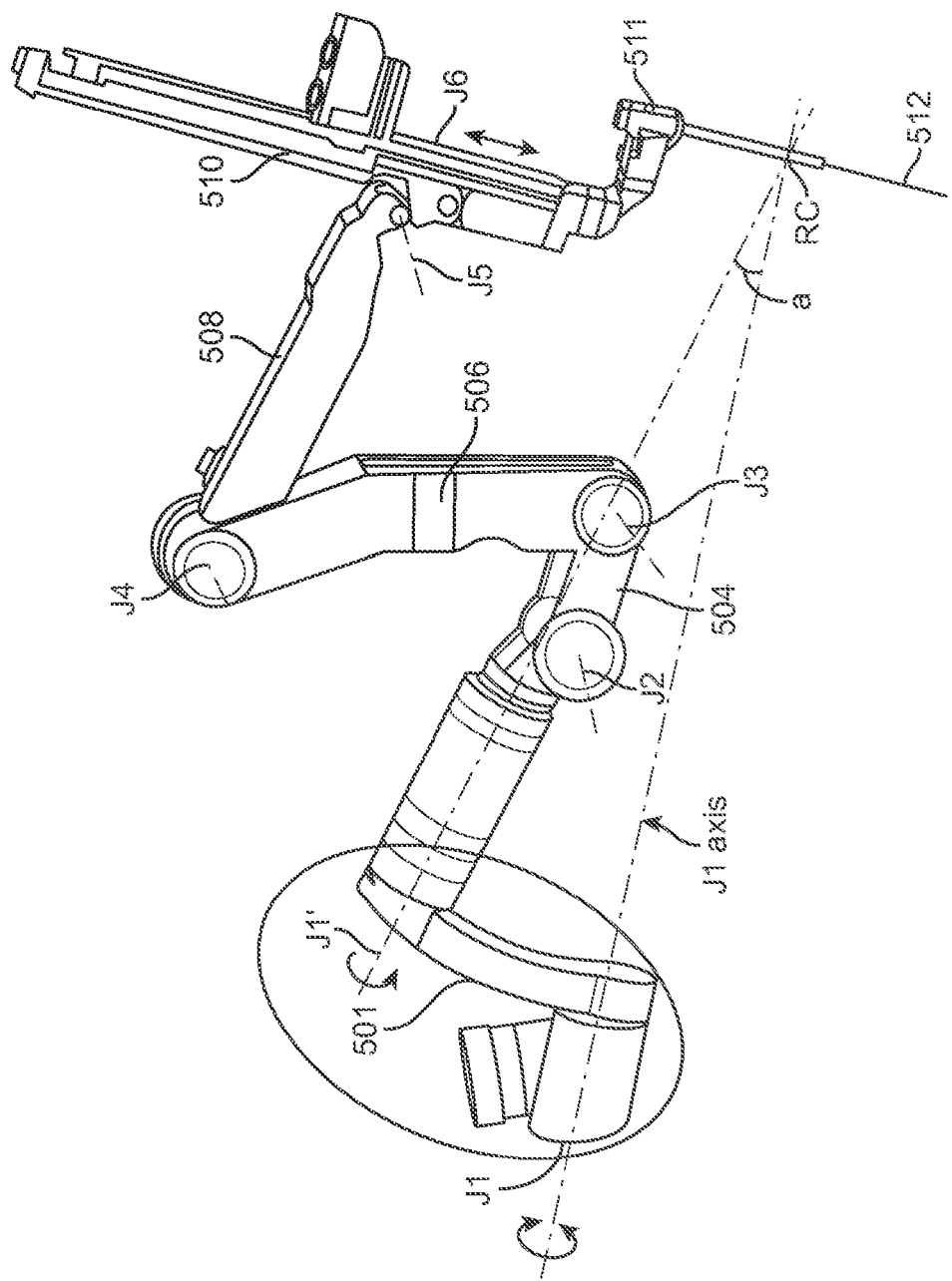
FIG. 7A shows example manipulator arms having a proximal revolute joint that revolves the manipulator arm about an axis of a proximal revolute joint.
Figure 7B:
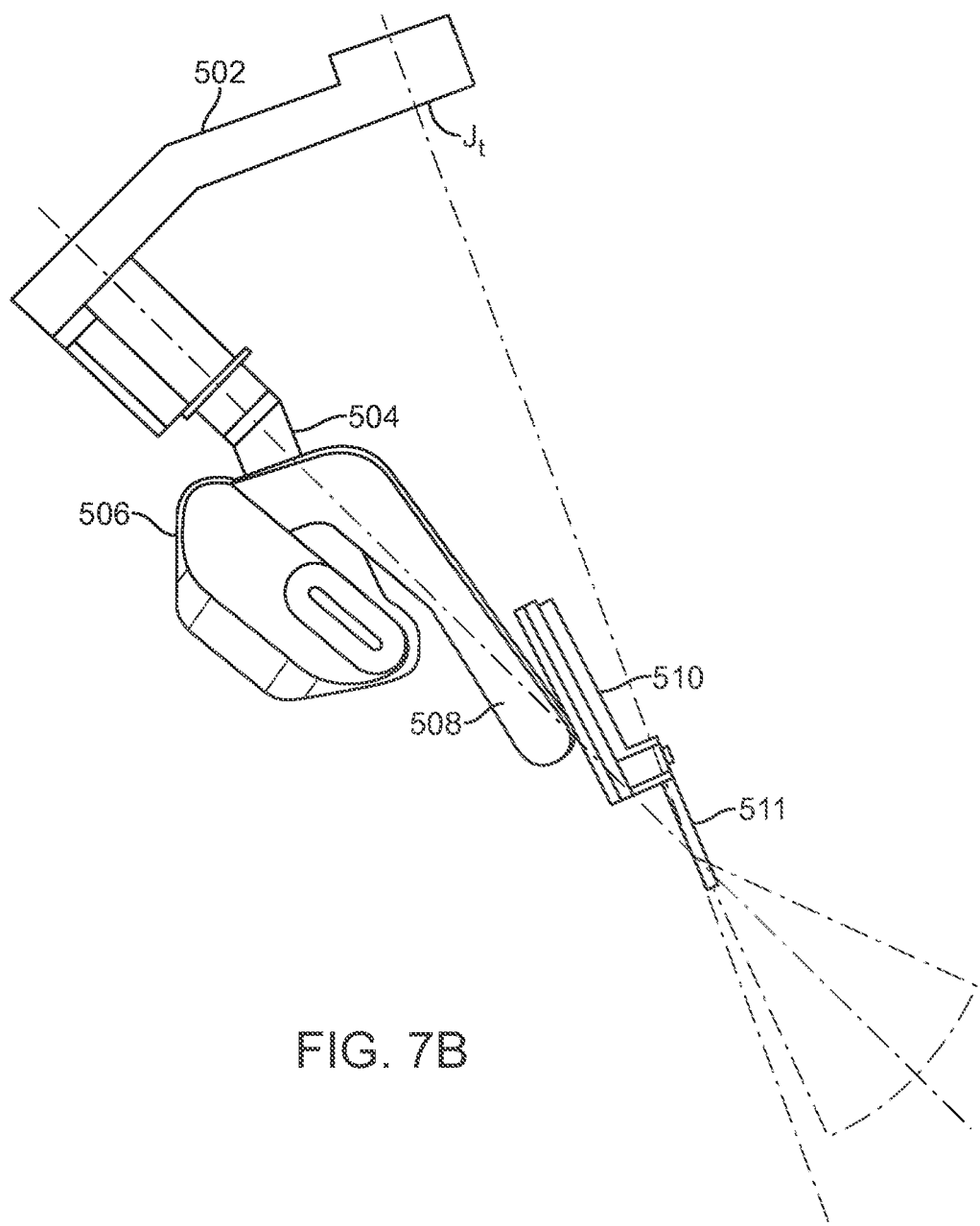
FIG. 7B shows an example manipulator arm and the associated range of motion and cone of silence, the exemplary manipulator arm having a proximal revolute joint that revolves the manipulator arm around an axis of a proximal revolute joint the movement of which can be used to mitigate the depicted cone of silence.

FIGS. 7A-7B illustrate an additional redundant joint for use with exemplary manipulator arms—a first joint coupling a proximal portion of the manipulator arm to the base. The first joint is a proximal revolute joint J1 that revolves the manipulator arm about a joint axis of joint J1. The proximal revolute J1 includes a link 501 that offsets joint J1' from the proximal revolute J1 by a pre-determined distance or angle. The link 501 can be a curved linkage, as shown in FIG. 7A, or a linear or angled linkage, as shown in FIG. 7B. Typically, the joint axis of the joint J1 is aligned with the remote center RC or insertion point of the tool tip, as shown in each of FIG. 7A. In an exemplary embodiment, the joint axis of joint J1 passes through the remote center, as does each other revolute joint axis in the manipulator arm, to prevent motion at the body wall and can therefore be moved during surgery. The axis of joint J1 is coupled to a proximal portion of the arm so it can be used to change the position and orientation of the back of the arm. In general, redundant axes, such as this, allow the instrument tip to follow the surgeon's commands while simultaneously avoiding collisions with other arms or patient anatomy. In one aspect, the proximal revolute J1 is used solely to change the mounting angle of the manipulator with respect to the floor. This angle is important in order to 1) avoid collisions with external patient anatomy and 2) reach anatomy inside the body. Typically, the angle α between the proximal link of the manipulator attached to the proximal revolute joint J1 and the axis of the proximal revolute is about 15 degrees.

FIG. 7B illustrates the relationship of the proximal revolute joint J1 and its associated joint axis and the cone of silence in an exemplary manipulator arm. The joint axis of the proximal revolute joint J1 may pass through the cone of silence or may be completely outside of the cone of silence. By revolving the manipulator arm about the axis of the proximal revolute J1, the cone of silence can be reduced (in an embodiment where the joint J1 axis passes through the cone of silence), or can be effectively eliminated (in an embodiment where the proximal revolute joint axis extends completely outside the cone of silence). The distance and angle of the link 501 determines the position of the joint J1 axis relative to the cone of silence.

Figure 8:
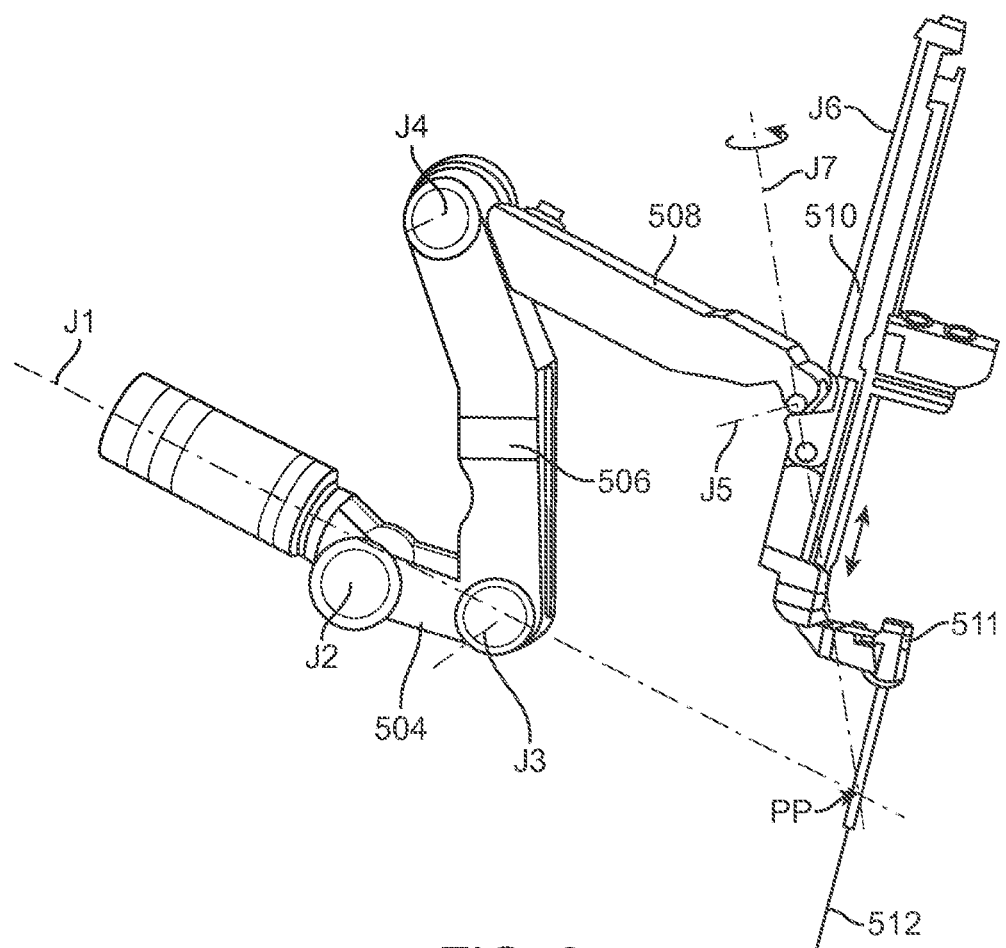
FIG. 8 shows an example manipulator arm having a revolute joint near the distal instrument holder.
Figure 9:
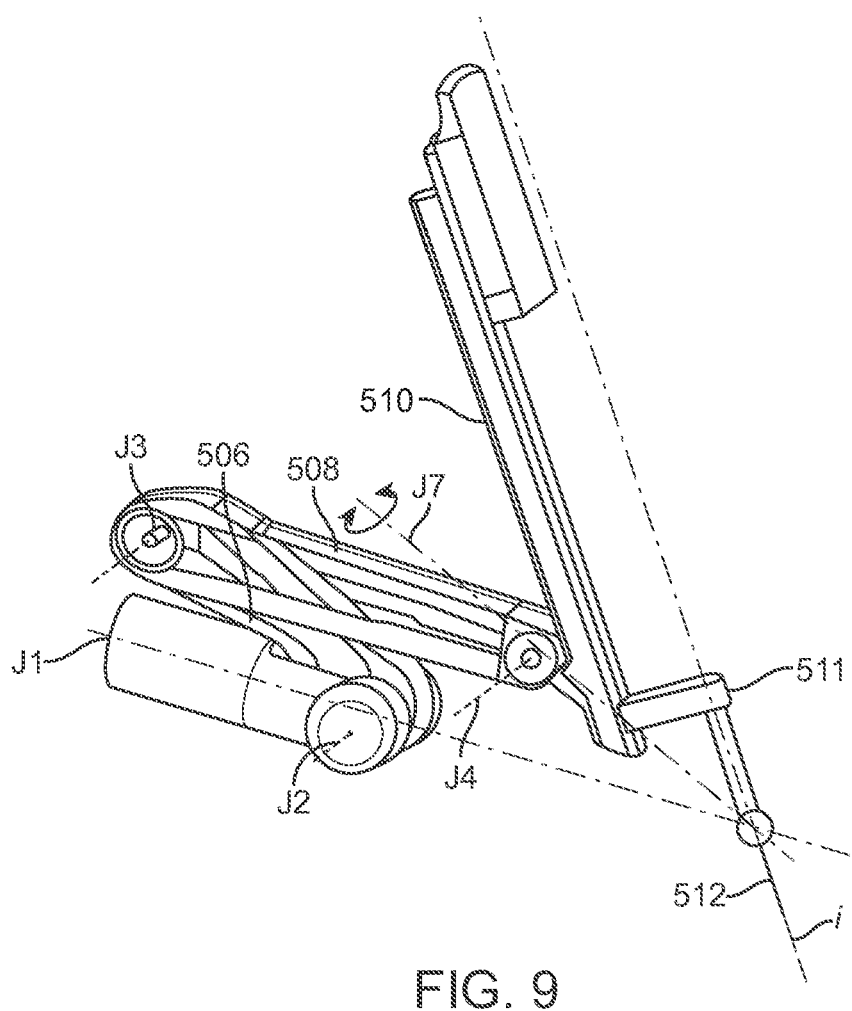
FIG. 9 shows an example manipulator arm having a revolute joint near the distal instrument holder that revolves or twists the instrument holder about the joint axis.
Figure 10A:
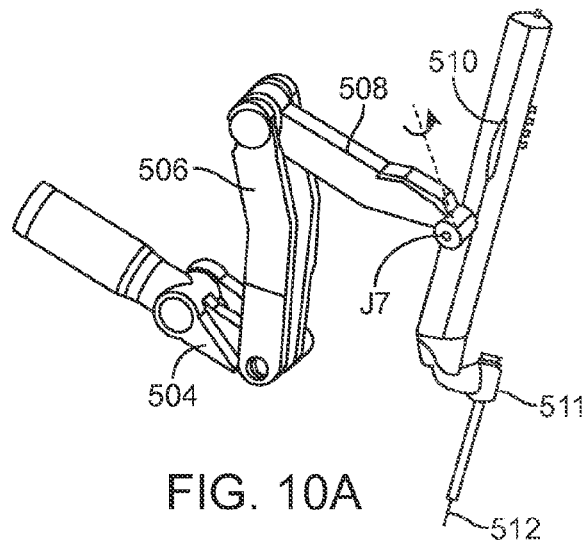
FIGS. 10A-10C show sequential views of an exemplary manipulator arm having a revolute joint near a distal instrument holder as the joint is moved throughout its range of joint movement.
Figure 10B:
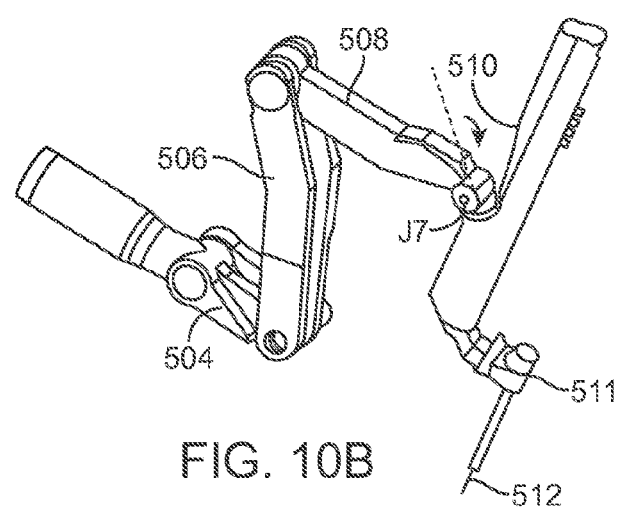
Figure 10C:
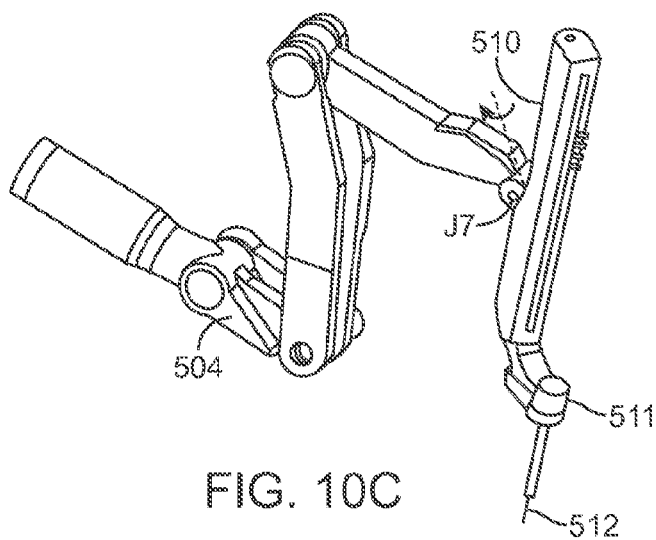

FIG. 8 illustrates another type of redundant joint for use with exemplary manipulator arms, a distal revolute joint J7 coupling the instrument holder 510 to a distal link of the manipulator arm 508. The distal revolute joint J7 allows the system to twist the instrument holder 510 about the joint axis, which typically passes through the remote center or insertion point. Ideally, the revolute joint is located distally on the arm and is therefore particularly well suited to moving the orientation of the insertion axis. The addition of this redundant axis allows the manipulator to assume multiple positions for any single instrument tip position. In general, redundant axes, such as this, allow the instrument tip to follow the surgeon's commands while simultaneously avoiding collisions with other arms or patient anatomy. Because the distal revolute joint J7 has the ability to move the insertion axis closer to the yaw axis, it is able to increase arm pitch back range of motion. The relationship between the axis of the distal revolute joint J7, the yaw axis of J1' and the insertion axis of tool tip is shown in FIG. 9. FIGS. 10A-10C show the sequential movement of the J7 and how it shifts the insertion axis of tool tip from side to side.

Figure 11A:
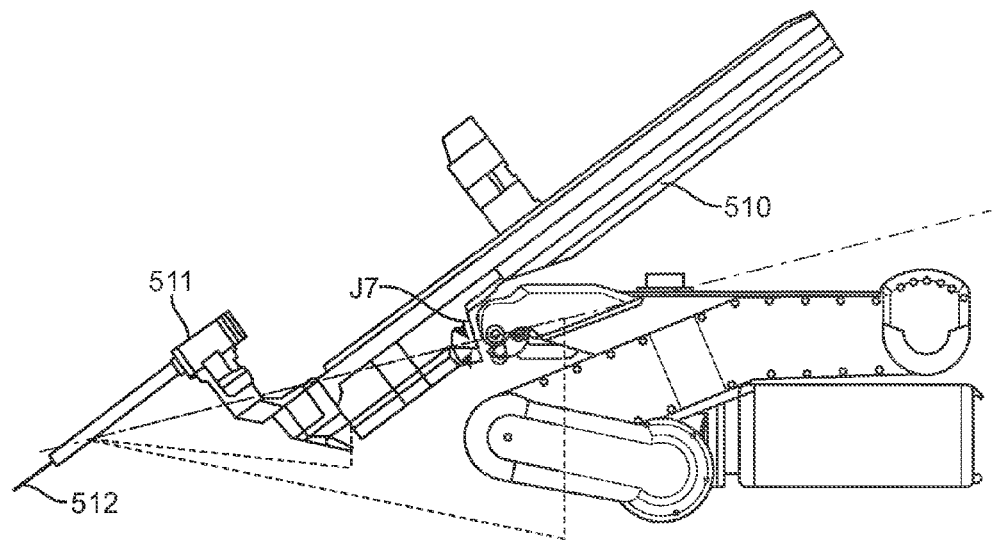
FIGS. 11A-11B show the revolved profile of an exemplary manipulator arm having a distal revolute joint when the angular displacement of the joint is 0° versus an angular displacement of 90°, respectively.
Figure 11B:
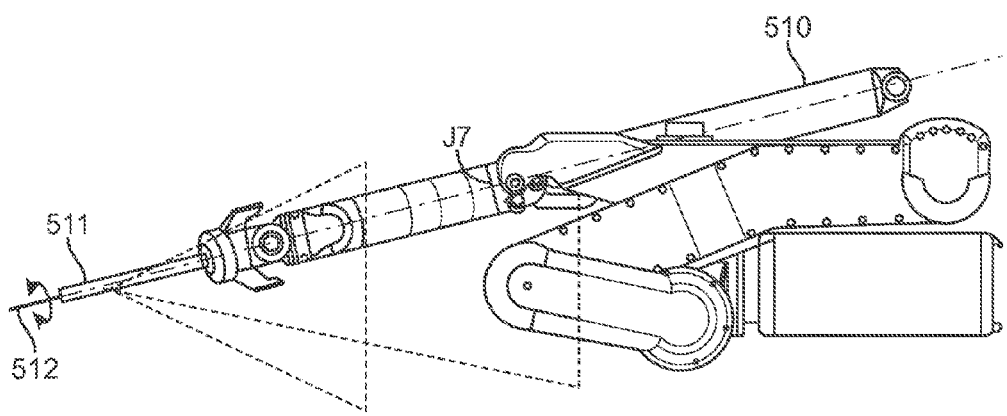

Another advantage of the distal revolute joint J7 is that it may reduce the patient clearance cone, which is the swept volume of the distal portion of the manipulator arm proximal of the insertion point which must clear the patient to avoid collision between the patient and the instrument holder or distal linkages of the manipulator arm. FIG. 11A illustrates the patient clearance cone of the proximal portion of the manipulator arm while the angular displacement of the distal revolute joint remains at 0°. FIG. 11B illustrates the reduced patient clearance cone of the proximal portion of the manipulator arm while the distal revolute joint is shown having an angular displacement of 90° about its axis. Thus, in procedures having minimal patient clearance near the insertion point, use of the joint J7 in accordance with the present invention may provide additional clearance while maintaining the remote center location or the position of the end effector as desired.

FIGS. 12A-12C illustrate another type of redundant joint for use with exemplary manipulator arms, a proximal joint that translates or revolves the manipulator arm about an axis. In many embodiments, this proximal translatable joint translates a proximal joint of the manipulator, such as joint J1 or J1', along a path so as to reduce or eliminate the cone of silence by shifting or rotating the range of motion of the manipulator arm to provide for better conditioning and improved maneuverability of the manipulator arm. The translatable joint may include a circular path, such as shown in joint J1" in FIGS. 12A-12D, or may include a semi-circular or arcuate path. Generally, the joint revolves the manipulator arm about an axis of the translatable joint that intersects with the remote center RC about which the shaft of the tool 512 extending through cannula 511 pivots. In the embodiments shown this axis of J1" is a vertical axis, although in various other embodiments the axis may be at an angle or horizontal.

In some embodiments, the manipulator arm 500 may include any or all of the proximal and distal revolute joint, a proximal translatable joint and a parallelogram configuration of the distal linkages. Use of any or all of these features provide additional redundant degrees of freedom and facilitate reconfiguration in accordance with the present invention so as to provide for a better "conditioned" manipulator assembly by increasing the angles between linkages thereby improving the dexterity and motion of the manipulator. The increased flexibility of this exemplary manipulator can also be used to optimize the kinematics of the manipulator linkage so as to avoid joint limits, singularities, and the like.

In an example embodiment, the joint movements of the manipulator are controlled by driving one or more joints by a controller using motors of the system, the joints being driven according to coordinated and joint movements calculated by a processor of the controller. Mathematically, the controller may perform at least some of the calculations of the joint commands using vectors and/or matrices, some of which may have elements corresponding to configurations or velocities of the joints. The range of alternative joint configurations available to the processor may be conceptualized as a joint space. The joint space may, for example, have as many dimensions as the manipulator has degrees of freedom, and a particular configuration of the manipulator may represent a particular point in the joint space, with each coordinate corresponding to a joint state of an associated joint of the manipulator.

In an example embodiment, the system includes a controller in which a commanded position and velocity of a feature in the work-space, denoted here as its Cartesian space, are inputs. The feature may be any feature on the manipulator or off the manipulator which can be used as a control frame to be articulated using control inputs. An example of a feature on the manipulator, used in many examples described herein, would be the tool-tip. Another example of a feature on the manipulator would be a physical feature which is not on the tool-tip, but is a part of the manipulator, such as a pin or a painted pattern. An example of a feature off the manipulator would be a reference point in empty space which is exactly a certain distance and angle away from the tool-tip. Another example of a feature off the manipulator would be a target tissue whose position relative to the manipulator can be established. In all these cases, the end effector is associated with an imaginary control frame which is to be articulated using control inputs. However, in the following, the "end effector" and the "tool tip" are used synonymously. Although generally, there is no closed form relationship which maps a desired Cartesian space end effector position to an equivalent joint-space position, there is generally a closed form relationship between the Cartesian space end effector and joint-space velocities. The kinematic Jacobian is the matrix of partial derivatives of Cartesian space position elements of the end effector with respect to joint space position elements. In this way, the kinematic Jacobian captures the kinematic relationship between the end effector and the joints. In other words, the kinematic Jacobian captures the effect of joint motion on the end effector. The kinematic Jacobian (J) can be used to map joint-space velocities (dq/dt) to Cartesian space end effector velocities (dx/dt) using the relationship below:

$$dx/dt = J dq/dt$$

Thus, even when there is no closed-form mapping between input and output positions, mappings of the velocities can iteratively be used, such as in a Jacobian-based controller to implement a movement of the manipulator from a commanded user input, however a variety of implementations can be used. Although many embodiments include a Jacobian-based controller, some implementations may use a variety of controllers that may be configured to access the Jacobian of the manipulator arm to provide any of the features described herein.

One such implementation is described in simplified terms below. The commanded joint position is used to calculate the Jacobian (J). During each time step (Δt) a Cartesian space velocity (dx/dt) is calculated to perform the desired move ($dx_{des}/dt$) and to correct for built up deviation (Δx) from the desired Cartesian space position. This Cartesian space velocity is then converted into a joint-space velocity (dq/dt) using the pseudo-inverse of the Jacobian ($J^{\#}$). The resulting joint-space commanded velocity is then integrated to produce joint-space commanded position (q). These relationships are listed below:

$$dx/dt = dx_{des}/dt + k\Delta x \quad (1)$$

$$dq/dt = J^{\#} dx/dt \quad (2)$$

$$q_i = q_{i-1} + dq/dt \, \Delta t \quad (3)$$

The pseudo-inverse of the Jacobian (J) directly maps the desired tool tip motion (and, in some cases, a remote center of pivotal tool motion) into the joint velocity space. If the manipulator being used has more useful joint axes than tool tip degrees of freedom (up to six), (and when a remote center of tool motion is in use, the manipulator should have an additional 3 joint axes for the 3 degrees of freedom associated with location of the remote center), then the manipulator is said to be redundant. A redundant manipulator's Jacobian includes a "null-space" having a dimension of at least one. In this context, the "null-space" of the Jacobian (N(J)) is the space of joint velocities which instantaneously achieves no tool tip motion (and when a remote center is used, no movement of the pivotal point location); and "null-motion" is the combination, trajectory or path of joint positions which also produces no instantaneous movement of the tool tip and/or location of the remote center. Incorporating or injecting the calculated null-space velocities into the control system of the manipulator to achieve the desired reconfiguration of the manipulator (including any reconfigurations described herein) changes above equation (2) to the following:

$$dq/dt = dq_{perp}/dt + dq_{null}/dt \quad (4)$$

$$dq_{perp}/dt = J^{\#} dx/dt \quad (5)$$

$$dq_{null}/dt = (1 - J^{\#} J) z = V_n V_n^T z = V_n \alpha \quad (6)$$

The joint velocity according to Equation (4) has two components: the first being the null-perpendicular-space component, the "purest" joint velocity (shortest vector length) which produces the desired tool tip motion (and when the remote center is used, the desired remote center motion) and the second being the null-space component. Equations (2) and (5) show that without a null-space component, the same equation is achieved. Equation (6) starts with a traditional form for the null-space component on the left, and on the far right side, shows the form used in an exemplary system, wherein $V_n$ is the set of orthonormal basis vectors for the null-space, and $\alpha$ are the coefficients for blending those basis vectors. In some embodiments, $\alpha$ is determined by control parameters, variables or setting, such as by use of knobs or other control means, to shape or control the motion within the null-space as desired.

Figure 13A:
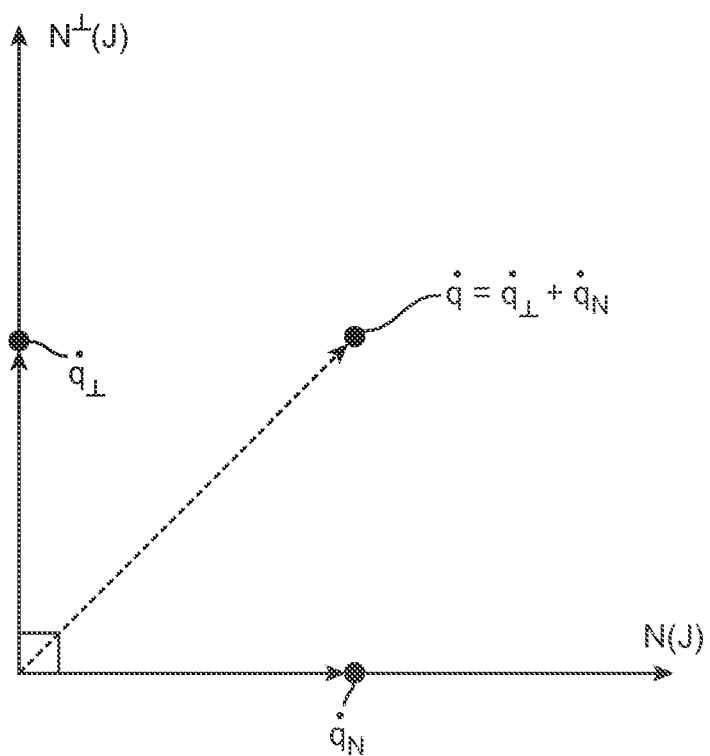
FIGS. 13A-13B graphically represent the relationship between the null-space and the null-perpendicular-space of the Jacobian of an example manipulator assembly.
Figure 13B:
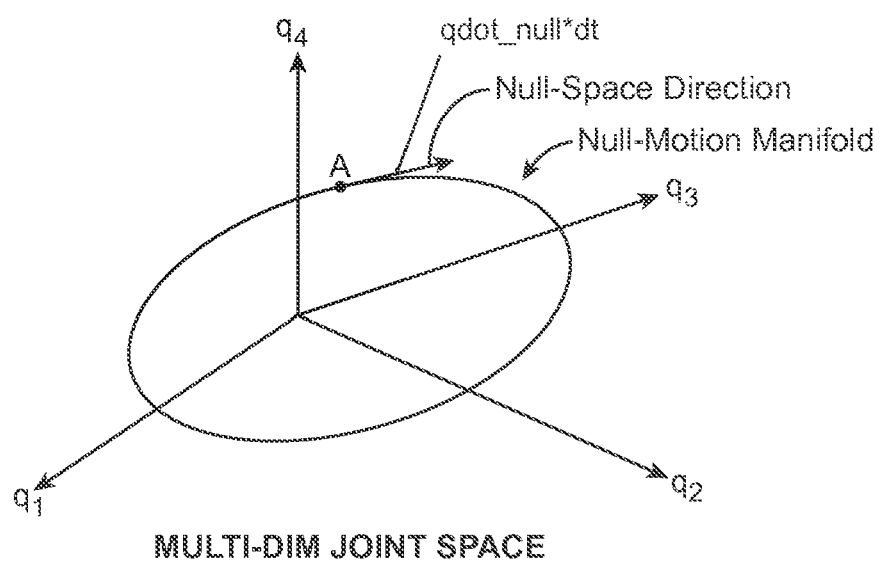

FIGS. 13A-13B graphically illustrate the relationship between the mill-space of the Jacobian and the null-perpendicular-space of the Jacobian of an exemplary manipulator arm. FIG. 13A shows a two-dimensional schematic showing the null-space along the horizontal axis, and the null-perpendicular-space along the vertical axis, the two axes being orthogonal to one another. The diagonal vector represents the sum of a velocity vector in the null-space and a velocity vector in the null-perpendicular-space, which is representative of Equation (4) above.

FIG. 13B graphically illustrates the relationship between the null-space and the null-motion manifold within a four-dimensional joint space, shown as the "null-motion manifold." Each arrow (q1, q2, q3, and q4) representing a principal joint axis. The closed curve represents a null-motion manifold which is a set of joint-space positions which instantaneously achieves the same end effector position. For a given point A on the curve, since the null-space is a space of joint velocities which instantaneously produce no movement of the end effector, the null-space is parallel to the tangent of the null-motion manifold at point A.

In the first approach, the Joint-space weighted pseudo-inverse approach referenced above, the system calculates a weighted pseudo-inverse of a Jacobian matrix. For example, using the chain rule along with the definition of the Jacobian, the result can be obtained according to the following equations, in which W is a weight matrix used to weight the joint velocities and $(\;)^{\#}$ is the pseudo-inverse solution:

$$dx/dt = J^* dq/dt \quad (7)$$

$$dx/dt = J^* W^* W^{(-1)} * dq/dt \quad (8)$$

$$W^{(-1)} * dq/dt = (J^* W)^{\#} * dx/dt \quad (9)$$

$$dq/dt = W^* (J^* W)^{\#} * dx/dt \quad (10)$$

In another approach, a Cart-space weighted pseudo-inverse approach, the following equations may be used:

$$dx/dt = J^* dq/dt$$

$$W^* dx/dt = W^* J^* dq/dt$$

$$dq/dt = (W^* J)^{\#} (W^* dx/dt)$$

In one example, this approach may be utilized by setting W=diagonal([1 1 0 1 1 1]). This causes the 3rd Cart-space velocity element, namely translations along Z, to have 0 impact on dq/dt, and therefore the resulting joint velocities produce 0 translations along end effector Z.

Although the weighted joint velocities can be obtained by use of the above equations, there may be certain drawbacks associated with this approach. For example, should various other tasks associated with the manipulator movement use unweighted joint velocities of a singular value decomposition calculation, such as null-space basis vectors used for various other algorithms, this approach may require an additional singular value decomposition calculation for these various other tasks.

In the second approach, referenced above, to minimize the required number of computations, the system may be configured to apply a weighting on the joint velocities based on unweighted joint velocities, thereby requiring only a single singular value decomposition for each kernel cycle. Thus, various other tasks or movement could utilize the unweighted joint velocities while a weighting is applied to the joint velocities to provide the desired joint state or movement of the first set of joints during commanded movement. In this approach, the dq/dt from the pseudo-inverse of the Jacobian, such as may be obtained from equations (2) or (5) above, is applied to an anisotropic surface representing the weighting in the joint velocity space to determine a gradient. Then, the difference between the pseudo-inverse solution and the gradient of the surface at the pseudo-inverse solution becomes the weighting correction, which is projected onto the null-space to determine the weighted joint velocities.

Figure 14:
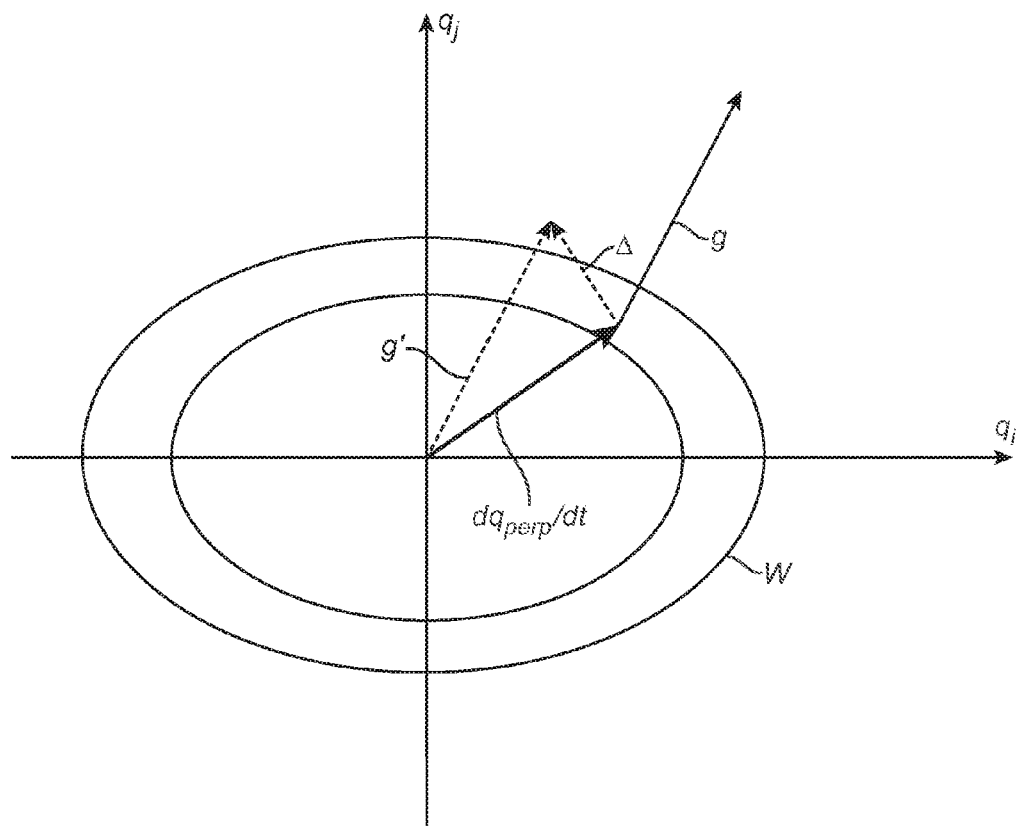
FIG. 14 graphically depicts the method of calculating weighted joint velocities within the joint space using a pseudo-inverse of the Jacobian and a potential function gradient.

FIG. 14 graphically illustrates an example of the second approach. The weighting W is depicted as an anisotropic paraboloid within the joint space. The vector labeled dq/dt is the original pseudo-inverse solution calculated in response to a commanded movement of the tool tip and/or remote center. The gradient, g, of the anisotropic paraboloid representing the joint velocity weight is moved to the original (shown as g') so as to determine the difference Δ between the dw/dt vector and the gradient, which is subsequently projected onto the null-space of the joints to determine the $dq_{null}/dt$, which is used to determine the weighted joint velocities. The idealized joint velocity vector may not always be achievable such that the resulting vector, $dq_{null}/dt + dq_{perp}/dt$ approaches the joint movement defined by the weighting.

This approach may be accomplished by use of the following equations, in which C is the cost function defined by the parabaloid, g is the gradient, and $V_n$ denotes the null-space basis vectors.

$$C = \tfrac{1}{2}\|W^*dq_{perp}/dt\|^2 = \tfrac{1}{2}(dq_{perp}/dt)^T * W^T * W * dq_{perp}/dt \quad (11)$$

$$g_{(dq_{perp}/dt)}C = W^T * W * dq_{perp}/dt \quad (12)$$

Typically, in the gradient notation above, the expression in the parentheses must be lowered to indicate that the gradient is taken relative to the expression. So $g_{(x)}y = (dy/dx)^T$ The correction, which is the difference between (12) and the original $dq_{perp}/dt$ is:

$$\Delta = W^T * W * dq_{perp}/dt - dq_{perp}/dt = (W^T * W - 1) * dq_{perp}/dt \quad (13)$$

Projecting Δ onto the null-space, with basis vectors $V_n$ yields:

$$dq_{null}/dt = V_n * V_n^T * \Delta = V_n + V_n^T * (W^T * W - 1) * dq_{perp}/dt \quad (14)$$

Since $dq_{perp}/dt$ is the pseudo-inverse solution, its projection onto the null-space is zero, hence:

$$V_n * V_n^T * dq_{perp}/dt = 0 \quad (15)$$

$$dq_{null}/dt = V_n * V_n^T * W^T * W * dq_{perp}/dt \quad (16)$$

By use of the above equations, the desired weighted joint velocities can be a diagonalized matrix with zeroes along the diagonal and the unweighted singular value decomposition can be shared by multiple users for various tasks, including for use in any of the above algorithms. By setting the weights for the joints, equation (16) can be used to generate a null-space vector for adjusting the velocity profile of the joints according to the weighted joint velocities with fairly minimal computations.

Alternatively, in certain aspects, an augmented Jacobian that incorporates a potential function gradient and is applied to the Cartesian Space end effector velocities may be used. The augmentation of the Jacobian calculates the joint velocities as desired. It is understood that in referring to calculating joint movements using the Jacobian, such calculations may include the augmented Jacobian approach. In accordance with the augmented Jacobian approach, the following equations may be used, although it is appreciated that column vectors may be used:

$$dx/dt = J * dq/dt$$

$$y = h(q)$$

$$dy/dt = \partial h / \partial q * dq/dt$$

$$[dx/dt^T \, dy/dt^T]^T = [J^T \, \partial h / \partial q^T]^T * dq/dt$$

$$d(x;y)/dt = [J;h'] * dq/dt$$

$$dq/dt = [J;h']^\# d(x;y)/dt$$

This approach may be illustrated in two examples, as follows:

In a first example: Set dy/dt=0, ∂h/∂q=[0 0 1 −2 0 0 0], which tries to force the velocity of joint 3 to equal 2× velocity of joint 4.

In as second example: Set dy/dt=0, ∂h/∂q=[0 0 1 0 0 0 0], which tries to force the velocity of joint 3 to equal 0.

Figure 15:
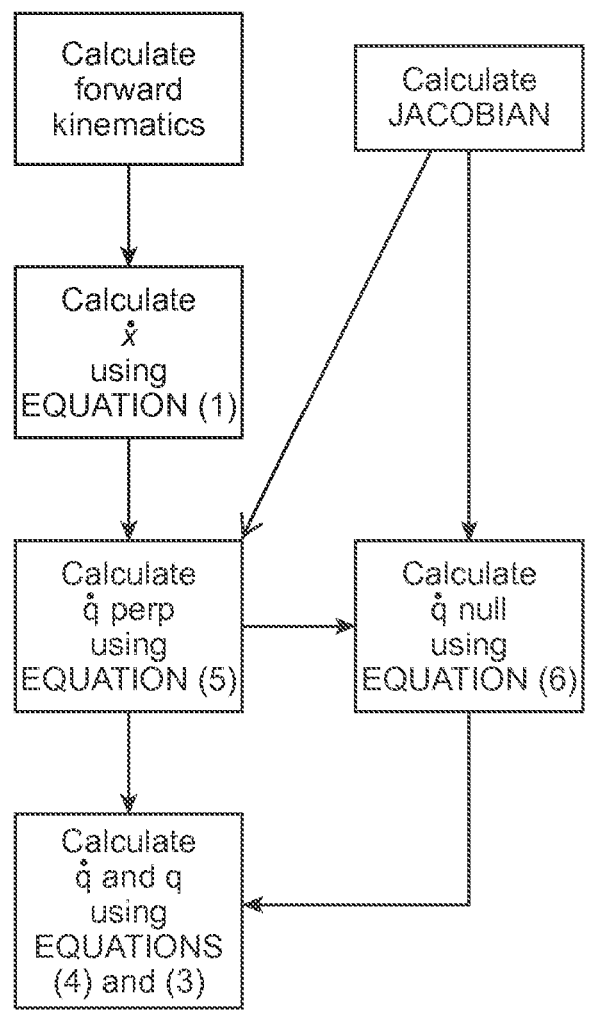
FIG. 15 illustrate a block diagram used to implement general algorithms in an example manipulator assembly.

FIG. 15 shows a simplified schematic of the required blocks needed to implement the general algorithms to control the patient side cart joint states, in relation to the equations discussed above. According to the method of FIG. 15, the system calculates the forward kinematics of the manipulator arm, then calculates dx/dt using Equation (1), calculates $dq_{perp}/dt$ using Equation (5), and then calculates $dq_{null}/dt$ from z which may depend on $dq_{perp}/dt$ and the Jacobian using Equation (6). From the calculated $dq_{perp}/dt$ and $dq_{null}/dt$, the system then calculates dq/dt and q using Equations (4) and (3), respectively, thereby providing the calculated movement by which the controller can effect the desired reconfiguration of the manipulator while maintaining the desired state of the end effector (and/or location of the remote center).

Figure 16:
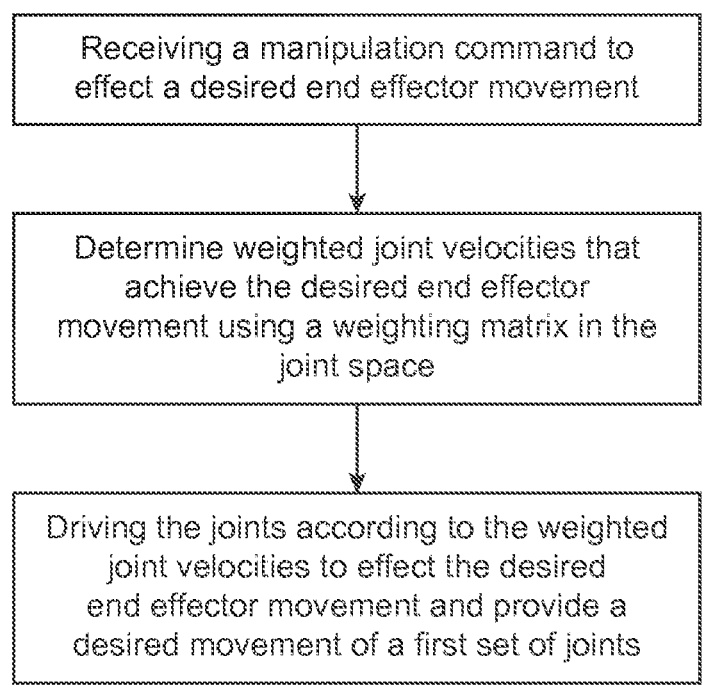
FIGS. 16-17 illustrate block diagrams of example methods in accordance with the present invention.
Figure 17:
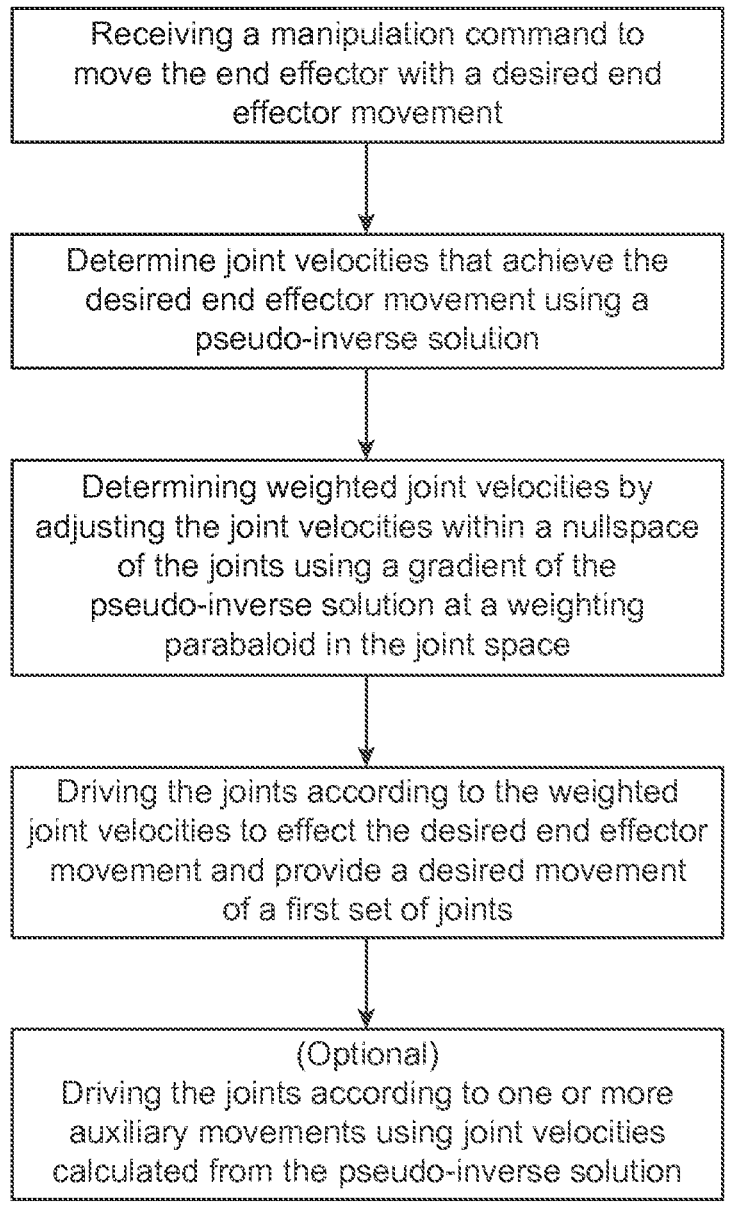

FIGS. 16-17 show flow charts of example methods in accordance with the present invention. In an example method, as shown in FIG. 16, the system includes determining weighted joint velocities using a weighting matrix that corresponds to a desired movement of a first set of joints in response to a manipulation command input by a user to move the end effector according to a desired end effector movement. The system then drives the joints according to the weighted joint velocities so as to effect the desired end effector movement and provide the desired movement of the first set of joints. As shown in FIG. 17, the method may further include determining joint velocities that achieve the commanded end effector movement using a pseudo-inverse solution. The weighted joint velocities can be calculated by adjusting the joint velocities using a potential function gradient of the pseudo-inverse solution and using a weighting matrix within the joint space, such as described above. The system drives the joints according to the weighted joint velocities to effect the desired end effector movement and provide the desired movement of a first set of joints. Optionally, the system may use the pseudo-inverse solution at a weighting surface to calculate joint velocities associated with one or more auxiliary tasks, such as commanded reconfiguration or collision avoidance, so that the joints can be driven to effect the auxiliary tasks during the commanded end effector movement while still providing the desired movement of the first set of joints.

While the example embodiments have been described in some detail for clarity of understanding and by way of example, a variety of adaptations, modifications, and changes will be obvious to those of skill in the art. Hence, the scope of the present invention is limited solely by the appended claims.

What is claimed is:

1. A method for moving a manipulator arm, the manipulator arm comprising a distal portion that supports an instrument that includes an end effector, a proximal portion coupled to a base, and a plurality of joints between the distal portion and the base, the plurality of joints providing sufficient degrees of freedom to allow a range of differing joint states for a given state of the end effector, the method comprising:

receiving a manipulation command to move the end effector with a desired end-effector movement;

determining an end-effector displacing movement of the plurality of joints to effect the desired end-effector movement by calculating joint velocities of the plurality of joints that achieve the desired end-effector movement;

determining an additional movement of the plurality of joints by calculating weighted joint velocities based on a weighting within a joint space of the plurality of joints, the weighting being applied to the calculated joint velocities of the plurality of joints for the end-effector displacing movement, and the additional movement corresponding to the end-effector not being in motion; and driving the plurality of joints according to a combination of the end-effector displacing movement of the plurality of joints and the additional movement of the plurality of joints.

2. The method of claim 1, wherein the additional movement is directed towards a desired value comprising a value selected from the group consisting of: a joint state, a combination of joint states, a relative joint state, a range of joint states, a profile of joint states, and a kinetic energy of joint states.

3. The method of claim 1, wherein the weighted joint velocities for the additional movement of the plurality of joints lie in a null space of a Jacobian of the manipulator arm.

4. The method of claim 1, wherein calculating the weighted joint velocities includes projecting values based on the joint velocities of the plurality of joints for the end-effector displacing movement onto a null space of a Jacobian of the manipulator arm.

5. The method of claim 1, wherein the weighting comprises a weighting matrix in the joint space of the plurality of joints.

6. The method of claim 1, wherein the weighting comprises a quadratic surface within the joint space of the plurality of joints.

7. The method of claim 1, wherein the weighting comprises a paraboloid surface within the joint space of the plurality of joints.

8. The method of claim 1, wherein
determining the end effector displacing movement comprises calculating a pseudo-inverse solution of a Jacobian of the manipulator arm; and
determining the additional movement comprises calculating a difference between the pseudo-inverse solution and a potential function gradient of the pseudo-inverse solution.

9. The method of claim 8, wherein determining the additional movement further comprises projecting the difference onto a null space of the Jacobian to determine the weighted joint velocities of the additional movement.

10. A system comprising:
a manipulator arm comprising a distal portion that is configured to releasably support an instrument that includes an end effector, a proximal portion coupled to a base, and a plurality of joints between the distal portion and the base, the plurality of joints providing sufficient degrees of freedom to allow a range of joint states for a given state of the end effector;
an input device configured to receive a manipulation command to move the end effector with a desired end-effector movement; and
a processor that couples the input device to the manipulator arm, the processor being configured to perform operations including:
determining an end-effector displacing movement of the plurality of joints to effect the desired end-effector movement by calculating joint velocities of the plurality of joints that achieve the desired end-effector movement;

determining an additional movement of the plurality of joints by calculating weighted joint velocities based on a weighting within a joint space of the plurality of joints, the weighting being applied to the calculated joint velocities of the plurality of joints for the end-effector displacing movement, and the additional movement corresponding to the end-effector not being in motion; and transmitting a command to the manipulator arm in response to the end effector displacing movement to drive the plurality of joints according to a combination of the end-effector displacing movement of the plurality of joints and the additional movement of the plurality of joints.

11. The system of claim 10, wherein the additional movement is directed towards a desired value comprising a value selected from the group consisting of: a joint state, a combination of joint states, a relative joint state, a range of joint states, a profile of joint states, and a kinetic energy of joint states.

12. The system of claim 10, wherein the weighted joint velocities for the additional movement of the plurality of joints lie in a null space of a Jacobian of the manipulator arm.

13. The system of claim 10, wherein calculating the weighted joint velocities includes projecting values based on the joint velocities of the plurality of joints for the end-effector displacing movement onto a null space of a Jacobian of the manipulator arm.

14. The system of claim 10, wherein the weighting comprises a weighting matrix in the joint space of the plurality of joints.

15. The system of claim 10, wherein the weighting comprises a quadratic surface within the joint space of the plurality of joints.

16. The system of claim 10, wherein the weighting comprises a paraboloid surface within the joint space of the plurality of joints.

17. The system of claim 10, wherein
determining the end effector displacing movement comprises calculating a pseudo-inverse solution of a Jacobian of the manipulator arm; and
determining the additional movement comprises calculating a difference between the pseudo-inverse solution and a potential function gradient of the pseudo-inverse solution.

18. The system of claim 17, wherein determining the additional movement further comprises projecting the difference onto a null space of the Jacobian to determine the weighted joint velocities of the additional movement.

19. A system comprising:
a manipulator arm comprising a distal portion that is configured to releasably support an instrument that includes an end effector, a proximal portion coupled to a base, and a plurality of joints between the distal portion and the base, the plurality of joints providing sufficient degrees of freedom to allow a range of joint states for a given state of the end effector;
an input device configured to receive a manipulation command to move the end effector with a desired end-effector movement; and
means for determining an end-effector displacing movement of the plurality of joints to effect the desired end-effector movement by calculating joint velocities of the plurality of joints that achieve the desired end-effector movement;

means for determining an additional movement of the plurality of joints by calculating weighted joint velocities based on a weighting within a joint space of the plurality of joints, the weighting being applied to the calculated joint velocities of the plurality of joints for the end-effector displacing movement, and the additional movement corresponding to the end-effector not being in motion; and a processor-based command unit that is configured to transmit a command to the manipulator arm in response to the end effector displacing movement to drive the plurality of joints according to a combination of the end-effector displacing movement of the plurality of joints and the additional movement of the plurality of joints.

20. The system of claim 19, wherein the additional movement is directed towards a desired value comprising a value selected from the group consisting of: a joint state, a combination of joint states, a relative joint state, a range of joint states, a profile of joint states, and a kinetic energy of joint states.

* * * * *